(12) United States Patent
Hodgkinson et al.

(10) Patent No.: US 10,786,255 B2
(45) Date of Patent: Sep. 29, 2020

(54) BUTTRESS ASSEMBLY FOR USE WITH SURGICAL STAPLING DEVICE

(71) Applicant: Covidien LP, Mansfield, MA (US)

(72) Inventors: Gerald Hodgkinson, Guilford, CT (US); Paul Scirica, Huntington, CT (US); Sally Carter, Nashua, NH (US); Richard Stevenson, Colchester, CT (US); Arthur Hislop, Plantsville, CT (US); Thomas Casasanta, Kensington, CT (US)

(73) Assignee: Covidien LP, Mansfield, MA (US)

( * ) Notice: Subject to any disclaimer, the term of this patent is extended or adjusted under 35 U.S.C. 154(b) by 437 days.

(21) Appl. No.: 14/808,187

(22) Filed: Jul. 24, 2015

(65) Prior Publication Data
US 2015/0327864 A1 Nov. 19, 2015

Related U.S. Application Data

(62) Division of application No. 13/325,428, filed on Dec. 14, 2011, now Pat. No. 9,113,885.

(51) Int. Cl.
A61B 17/068 (2006.01)
A61B 17/10 (2006.01)
(Continued)

(52) U.S. Cl.
CPC .......... A61B 17/105 (2013.01); A61B 17/068 (2013.01); A61B 17/1114 (2013.01);
(Continued)

(58) Field of Classification Search
USPC ........................................................ 606/151
See application file for complete search history.

(56) References Cited

U.S. PATENT DOCUMENTS 3,054,406 A 9/1962 Usher
3,079,606 A 3/1963 Bobrov et al.
(Continued)

FOREIGN PATENT DOCUMENTS

CA 2 667 434 A1 5/2008
CN 101310680 A 11/2008
(Continued)

OTHER PUBLICATIONS

Extended European Search Report corresponding to EP 13 19 4995.0, completed Jun. 5, 2014 and dated Jun. 16, 2014; (5 pp).
(Continued)

Primary Examiner — Michelle Lopez
Assistant Examiner — Chinyere J Rushing-Tucker
(74) Attorney, Agent, or Firm — Carter, DeLuca & Farrell LLP

(57) ABSTRACT

An apparatus for joining two hollow organ sections includes a staple cartridge component, an anvil component, a knife member, a buttress mount and a buttress member. The staple cartridge component includes a plurality of surgical staples in an annular array. The anvil component is movable relative to the staple cartridge component between spaced apart and approximated positions to adjustably clamp tissue. The knife member is movable relative to the staple cartridge component. The buttress mount is concentrically disposed at least partially within the lumen of the knife member. The buttress mount includes a plurality of spokes radially extending outward and a plurality of legs detachably secured with an inner wall of the knife member. The buttress member is secured with the plurality of spokes of the buttress mount. The buttress member is concentrically aligned with the plurality of surgical staples.

7 Claims, 19 Drawing Sheets

(51) Int. Cl.
*A61B 17/32* (2006.01)
*A61B 17/11* (2006.01)
*A61B 17/115* (2006.01)
*A61B 17/072* (2006.01)
*A61B 17/00* (2006.01)

(52) U.S. Cl.
CPC .......... *A61B 17/1155* (2013.01); *A61B 17/32* (2013.01); *A61B 17/07292* (2013.01); *A61B 2017/00473* (2013.01); *A61B 2017/1132* (2013.01)

(56) References Cited

U.S. PATENT DOCUMENTS

| | | | |
|---|---|---|---|
| 3,124,136 A | 3/1964 | Usher | |
| 3,364,200 A | 1/1968 | Ashton et al. | |
| 3,490,675 A | 1/1970 | Green et al. | |
| 3,499,591 A | 3/1970 | Green | |
| 3,797,494 A | 3/1974 | Zaffaroni | |
| 3,939,068 A | 2/1976 | Wendt et al. | |
| 3,948,666 A | 4/1976 | Kitanishi et al. | |
| 4,064,062 A | 12/1977 | Yurko | |
| 4,166,800 A | 9/1979 | Fong | |
| 4,282,236 A | 8/1981 | Broom | |
| 4,347,847 A | 9/1982 | Usher | |
| 4,354,628 A | 10/1982 | Green | |
| 4,416,698 A | 11/1983 | McCorsley, III | |
| 4,429,695 A | 2/1984 | Green | |
| 4,452,245 A | 6/1984 | Usher | |
| 4,473,077 A | 9/1984 | Noiles et al. | |
| 4,576,167 A | 3/1986 | Noiles | |
| 4,605,730 A | 8/1986 | Shalaby et al. | |
| 4,626,253 A | 12/1986 | Broadnax, Jr. | |
| 4,646,745 A | 3/1987 | Noiles | |
| 4,655,221 A | 4/1987 | Devereux | |
| 4,834,090 A | 5/1989 | Moore | |
| 4,838,884 A | 6/1989 | Dumican et al. | |
| 4,927,640 A | 5/1990 | Dahlinder et al. | |
| 4,930,674 A | 6/1990 | Barak | |
| 5,002,551 A | 3/1991 | Linsky et al. | |
| 5,005,749 A | 4/1991 | Aranyi | |
| 5,014,899 A | 5/1991 | Presty et al. | |
| 5,040,715 A | 8/1991 | Green et al. | |
| 5,057,334 A | 10/1991 | Vail | |
| 5,065,929 A | 11/1991 | Schulze et al. | |
| 5,119,983 A | 6/1992 | Green et al. | |
| 5,162,430 A | 11/1992 | Rhee et al. | |
| 5,205,459 A | 4/1993 | Brinkerhoff et al. | |
| 5,263,629 A | 11/1993 | Trumbull et al. | |
| 5,307,976 A | 5/1994 | Olson et al. | |
| 5,312,023 A | 5/1994 | Green et al. | |
| 5,314,471 A | 5/1994 | Brauker et al. | |
| 5,318,221 A | 6/1994 | Green et al. | |
| 5,324,775 A | 6/1994 | Rhee et al. | |
| 5,326,013 A | 7/1994 | Green et al. | |
| 5,332,142 A | 7/1994 | Robinson et al. | |
| 5,344,454 A | 9/1994 | Clarke et al. | |
| 5,392,979 A | 2/1995 | Green et al. | |
| 5,397,324 A | 3/1995 | Carroll et al. | |
| 5,405,072 A | 4/1995 | Zlock et al. | |
| 5,410,016 A | 4/1995 | Hubbell et al. | |
| 5,425,745 A | 6/1995 | Green et al. | |
| 5,441,193 A | 8/1995 | Gravener | |
| 5,441,507 A | 8/1995 | Wilk | |
| 5,443,198 A | 8/1995 | Viola et al. | |
| 5,468,253 A | 11/1995 | Bezwada et al. | |
| 5,484,913 A | 1/1996 | Stilwell et al. | |
| 5,503,638 A | 4/1996 | Cooper et al. | |
| 5,514,379 A | 5/1996 | Weissleder et al. | |
| 5,542,594 A | 8/1996 | McKean et al. | |
| 5,543,441 A | 8/1996 | Rhee et al. | |
| 5,549,628 A | 8/1996 | Cooper et al. | |
| 5,550,187 A | 8/1996 | Rhee et al. | |
| 5,575,803 A | 11/1996 | Cooper et al. | |
| 5,588,579 A | 12/1996 | Schnut et al. | |
| 5,645,915 A | 7/1997 | Kranzler et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,752,974 A | 5/1998 | Rhee et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,819,350 A | 10/1998 | Wang | |
| 5,833,695 A | 11/1998 | Yoon | |
| 5,843,096 A | 12/1998 | Igaki et al. | |
| 5,871,135 A | 2/1999 | Williamson, IV et al. | |
| 5,874,500 A | 2/1999 | Rhee et al. | |
| 5,895,412 A | 4/1999 | Tucker | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,957,363 A | 9/1999 | Heck | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,053,390 A | 4/2000 | Green et al. | |
| 6,063,097 A | 5/2000 | Oi et al. | |
| 6,080,169 A | 6/2000 | Turtel | |
| 6,093,557 A | 7/2000 | Pui et al. | |
| 6,099,551 A | 8/2000 | Gabbay | |
| 6,142,933 A | 11/2000 | Longo et al. | |
| 6,149,667 A | 11/2000 | Hovland et al. | |
| 6,152,943 A | 11/2000 | Sawhney | |
| 6,155,265 A | 12/2000 | Hammerslag | |
| 6,156,677 A | 12/2000 | Brown Reed et al. | |
| 6,165,201 A | 12/2000 | Sawhney et al. | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,270,530 B1 | 8/2001 | Eldridge et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,309,569 B1 | 10/2001 | Farrar et al. | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,399,362 B1 | 6/2002 | Pui et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,500,777 B1 | 12/2002 | Wiseman et al. | |
| 6,503,257 B2 | 1/2003 | Grant et al. | |
| 6,514,283 B2 | 2/2003 | DiMatteo et al. | |
| 6,514,534 B1 | 2/2003 | Sawhney | |
| 6,517,566 B1 | 2/2003 | Hovland et al. | |
| 6,551,356 B2 | 4/2003 | Rousseau | |
| 6,566,406 B1 | 5/2003 | Pathak et al. | |
| 6,590,095 B1 | 7/2003 | Schleicher et al. | |
| 6,592,597 B2 | 7/2003 | Grant et al. | |
| 6,605,294 B2 | 8/2003 | Sawhney | |
| 6,610,006 B1 | 8/2003 | Amid et al. | |
| 6,627,749 B1 | 9/2003 | Kumar | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,656,200 B2 | 12/2003 | Li et al. | |
| 6,669,735 B1 | 12/2003 | Pelissier | |
| 6,673,093 B1 | 1/2004 | Sawhney | |

(56) References Cited

U.S. PATENT DOCUMENTS

| | | |
|---|---|---|
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |

(56) References Cited

U.S. PATENT DOCUMENTS

| | | |
|---|---|---|
| 8,789,737 B2 | 7/2014 | Hodgkinson et al. |
| 8,814,888 B2 | 8/2014 | Sgro |
| 8,820,606 B2 | 9/2014 | Hodgkinson |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,486,215 B2 | 11/2016 | Olson et al. |
| 9,504,470 B2 | 11/2016 | Milliman |
| 9,572,576 B2 | 2/2017 | Hodgkinson et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,693,772 B2 | 7/2017 | Ingmanson et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,931,116 B2 | 4/2018 | Racenet et al. |
| 10,022,125 B2 | 7/2018 | (Prommersberger) Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0125676 A1 | 7/2003 | Swenson et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2005/0245965 A1* | 11/2005 | Orban, III ............ A61B 17/115 606/214 |
| 2005/0283256 A1 | 12/2005 | Sommerich et al. |
| 2006/0004407 A1 | 1/2006 | Hiles et al. |
| 2006/0008505 A1 | 1/2006 | Brandon |
| 2006/0025816 A1 | 2/2006 | Shelton |
| 2006/0085030 A1 | 4/2006 | Bettuchi et al. |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0190027 A1 | 8/2006 | Downey |
| 2006/0219752 A1 | 10/2006 | Arad et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |

(56) References Cited

U.S. PATENT DOCUMENTS

| | | |
|---|---|---|
| 2008/0200949 A1 | 8/2008 | Hiles et al. |
| 2008/0214695 A1 | 9/2008 | Pathak et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1* | 11/2008 | Bettuchi .......... A61B 17/07207 227/176.1 |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0031842 A1 | 2/2009 | Kawai et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0016855 A1 | 1/2010 | Ramstein et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331859 A1 | 12/2010 | Omori |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0034910 A1 | 2/2011 | Ross et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089220 A1 | 4/2011 | Ingmanson et al. |
| 2011/0089375 A1 | 4/2011 | Chan et al. |
| 2011/0125138 A1 | 5/2011 | Malinouskas et al. |
| 2011/0166673 A1 | 7/2011 | Patel et al. |
| 2011/0215132 A1 | 9/2011 | Aranyi et al. |
| 2011/0278346 A1 | 11/2011 | Hull et al. |
| 2011/0278347 A1 | 11/2011 | Olson et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0156289 A1 | 6/2012 | Blaskovich et al. |
| 2012/0187179 A1 | 7/2012 | Gleiman |
| 2012/0197272 A1 | 8/2012 | Oray et al. |
| 2012/0241491 A1 | 9/2012 | Aldridge et al. |
| 2012/0241499 A1 | 9/2012 | Baxter, III et al. |
| 2012/0253298 A1 | 10/2012 | Henderson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153634 A1* | 6/2013 | Carter .................. A61B 17/072 227/176.1 |
| 2013/0153635 A1 | 6/2013 | Hodgkinson |
| 2013/0153636 A1 | 6/2013 | Shelton, IV et al. |
| 2013/0153638 A1* | 6/2013 | Carter .................. A61B 17/072 227/179.1 |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0193186 A1 | 8/2013 | (Tarinelli) Racenet et al. |
| 2013/0193192 A1 | 8/2013 | Casasanta, Jr. et al. |
| 2013/0209659 A1 | 8/2013 | Racenet et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306707 A1 | 11/2013 | Viola et al. |
| 2013/0310873 A1 | 11/2013 | Stopek (nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0097224 A1 | 4/2014 | Prior |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1* | 8/2014 | Penna .............. A61B 17/07292 227/179.1 |
| 2014/0224686 A1 | 8/2014 | Aronhalt et al. |
| 2014/0239046 A1* | 8/2014 | Milliman ......... A61B 17/07292 227/180.1 |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1* | 4/2015 | Prescott ............. A61B 17/1155 227/179.1 |
| 2015/0122872 A1 | 5/2015 | Olson et al. |
| 2015/0133995 A1 | 5/2015 | Shelton, IV et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0231409 A1 | 8/2015 | Racenet et al. |

(56) References Cited

U.S. PATENT DOCUMENTS

| | | |
|---|---|---|
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Willman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | (Prommersberger) Stopek et al. |
| 2019/0021734 A1 | 1/2019 | Hodgkinson |
| 2019/0059878 A1 | 2/2019 | (Tarinelli) Racenet et al. |
| 2019/0083087 A1 | 3/2019 | Viola et al. |

FOREIGN PATENT DOCUMENTS

| | | |
|---|---|---|
| CN | 101332110 A | 12/2008 |
| DE | 1602563 U | 3/1950 |
| DE | 19924311 A1 | 11/2000 |
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 A1 | 8/2009 |
| EP | 2 090 244 A2 | 8/2009 |
| EP | 2 090 252 A2 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 A1 | 10/2010 |
| EP | 2 258 282 A2 | 12/2010 |
| EP | 2 292 276 A2 | 3/2011 |
| EP | 2 311 386 A2 | 4/2011 |
| EP | 2 436 348 A1 | 4/2012 |
| EP | 2 462 880 A2 | 6/2012 |
| EP | 2491867 A1 | 8/2012 |
| EP | 2 497 431 A1 | 9/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 98/38923 A1 | 9/1998 |
| WO | 99/45849 A1 | 9/1999 |
| WO | 03/082126 A1 | 10/2003 |
| WO | 03/088845 A2 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Extended European Search Report corresponding to EP 14 15 7195.0, completed Jun. 5, 2014 and dated Jun. 18, 2014; (9 pp).

Extended European Search Report corresponding to EP 14 15 6342.9, completed Jul. 22, 2014 and dated Jul. 29, 2014; (8 pp).

Extended European Search Report corresponding to EP 14 16 9739.1, completed Aug. 19, 2014 and dated Aug. 29, 2014; (7 pp).

Extended European Search Report corresponding to EP 14 15 7997.9, completed Sep. 9, 2014 and dated Sep. 17, 2014; (8 pp).

Extended European Search Report corresponding to EP 14 16 8904.2, completed Sep. 10, 2014 and dated Sep. 18, 2014; (8 pp).

Extended European Search Report corresponding to EP 13 19 4995.0, completed Jun. 5, 2014 and dated Oct. 13, 2014; (10 pp).

Extended European Search Report corresponding to EP 13 15 4571.7, completed Oct. 10, 2014 and dated Oct. 20, 2014; (8 pp).

Extended European Search Report corresponding to EP 14 18 1125.7, completed Oct. 16, 2014 and dated Oct. 24, 2014; (7 pp).

Extended European Search Report corresponding to EP 14 18 1127.3, completed Oct. 16, 2014 and dated Nov. 10, 2014; (8 pp).

Extended European Search Report corresponding to EP 14 19 0419.3, completed Mar. 24, 2015 and dated Mar. 30, 2015; (6 pp).

Extended European Search Report corresponding to EP 12 19 6902.6 dated Aug. 6, 2015; 7 pp.

Chinese Notification of Reexamination corresponding to counterpart Int'l Appln. No. CN 201010517292.8 dated Jun. 2, 2015.

Extended European Search Report corresponding to counterpart Int'l Appln. No. EP 14 15 2060.1 dated Aug. 14, 2015.

Office Action corresponding to counterpart Int'l Appln. No. JP 2014-216989 dated Sep. 11, 2015.

Canadian First Office Action corresponding to counterpart Int'l Appln. No. CA 2,686,105 dated Sep. 17, 2015.

Japanese Office Action corresponding to counterpart Int'l Appln. No. JP 2012-040188 dated Oct. 21, 2015.

(56) References Cited

OTHER PUBLICATIONS

European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
European Search Report corresponding to EP 05 02 2585.3, completed Jan. 25, 2006 and dated Feb. 3, 2006; (4 pp).
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 10 25 1437.9, completed Nov. 22, 2010 and dated Dec. 16, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 11 18 8309.6, completed Dec. 15, 2011 and dated Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 20131; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).

(56) References Cited

OTHER PUBLICATIONS

Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Chinese Office Action corresponding to counterpart Int'l Appln No. CN 201210129787.2 dated Aug. 24, 2015.
Chinese First Office Action corresponding to counterpart Int'l Appln. No. CN 2013107068710 dated Dec. 16, 2016.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 2013103036903 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
Japanese Office Action dated Jul. 27, 2016 in corresponding Japanese Patent Application No. 2012-268668 together with English transation, 7 pages.
Australian Patent Examination Report dated May 30, 2016 in corresponding Australian Patent Application No. 2012254977, 4 pages.
Japanese Office Action dated May 17, 2017 in corresponding Japanese Patent Application No. 2016-210267 together with English translation, 2 pages.
European Office Action corresponding to counterpart European Appln. No. EP 15 17 4146.9 dated May 15, 2017.
Japanese Office Action corresponding to counterpart Japanese Appln. No. JP 2013-154561 dated May 23, 2017.
European Office Action corresponding to counterpart European Appln. No. EP 12 19 4784.0 dated May 29, 2017.
Japanese Office Action corresponding to counterpart Japanese Appln. No. JP 2013-169083 dated May 31, 2017.
Australian Examination Report No. 1 corresponding to counterpart Australian Appln. No. AU 2013213767 dated Jun. 29, 2017.
Australian Examination Report No. 2 corresponding to counterpart Australian Appln. No. AU 2012261752 dated Jul. 7, 2017.
Australian Examination Report No. 1 corresponding to counterpart Australian Appln. No. AU 2013266989 dated Jul. 10, 2017.
Extended European Search Report corresponding to counterpart European Appln. No. EP 14 15 3609.4 dated Jul. 14, 2017.
Australian Examination Report No. 1 corresponding to counterpart Australian Appln. No. AU 2013234418 dated Jul. 14, 2017.
Extended European Search Report corresponding to counterpart European Appln. No. EP 14 15 3610.2 dated Jul. 17, 2017.
Australian Examination Report No. 1 corresponding to counterpart Australian Appln. No. AU 2014200109 dated Jul. 20, 2017.
Australian Examination Report No. 1 corresponding to counterpart Australian Appln. No. AU 2014200074 dated Jul. 20, 2017.
Japanese Office Action corresponding to counterpart Japanese Appln. No. JP 2013-250857 dated Aug. 17, 2017.
Japanese Office Action corresponding to counterpart Japanese Appln. No. JP 2013-229471 dated Aug. 17, 2017.
Australian Examination Report No. 1 corresponding to counterpart Australian Appln. No. AU 2014200793 dated Sep. 2, 2017.
Extended European Search Report corresponding to counterpart European Appln. No. EP 17 17 8528.0 dated Oct. 13, 2017.
Australian Examination Report No. 1 corresponding to counterpart Australian Appln. No. AU 2013234420 dated Oct. 24, 2017.
Japanese Office Action corresponding to counterpart Japanese Appln. No. JP 2013-175379 dated Oct. 20, 2017.
Japanese Office Action corresponding to counterpart Japanese Appln. No. JP 2013-147701 dated Oct. 27, 2017.
Extended European Search Report corresponding to counterpart European Appln. No. EP 17 17 5656.2 dated Nov. 7, 2017.
Japanese Office Action corresponding to counterpart Japanese Appln. No. JP 2014-009738 dated Nov. 14, 2017.
European Office Action corresponding to counterpart European Appln. No. EP 13 17 3986.4 dated Nov. 29, 2017.
Japanese Office Action corresponding to counterpart Japanese Appln. No. JP 2017-075975 dated Dec. 4, 2017.
European Office Action corresponding to counterpart European Appln. No. EP 13 19 79585 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.

(56) References Cited

OTHER PUBLICATIONS

Extended European Search Report corresponding to Patent Application EP 18192317.8 dated Dec. 20, 2018.
Extended European Search Report corresponding to Patent Application EP 18190154.7 dated Feb. 4, 2019.

* cited by examiner

BUTTRESS ASSEMBLY FOR USE WITH SURGICAL STAPLING DEVICE

CROSS-REFERENCE TO RELATED APPLICATIONS

The present application is a Divisional Application claiming the benefit of and priority to U.S. patent application Ser. No. 13/325,428, filed on Dec. 14, 2011, the entire content of each of which is incorporated herein by reference.

BACKGROUND

1. Technical Field

The present disclosure relates to a surgical instrument for applying surgical fasteners or staples to body tissue, and more particularly, to a surgical buttress for use with an end-to-end anastomosis stapling apparatus.

2. Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated shaft having a handle portion at a proximal end to actuate the instrument and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the instrument. Once the anvil shaft is secured to the instrument, the anvil is drawn into close approximation to the staple holding component. The instrument is then fired to cause the staples to pass through tissue of both sections of the organ and deform against the anvil. During the firing step, a circular knife is advanced to cut tissue inside the staple line, thereby establishing a passage between the two sections of the organ. After firing, the instrument is typically removed by withdrawing the anvil through the staple line, after which the surgeon will carefully inspect the surgical site to ensure a proper anastomosis has been achieved.

While circular staplers are helpful in a number of surgical procedures, it is desirable to reduce the incidents of anastomotic leak, tears of tissue during stapler extraction, bleeding, and other complications. In order to reduce such incidents, buttress or reinforcing materials have been utilized. However, due to the inherent difficulty in positioning and securing such materials with the instrument, a need exists for the buttress material that can be safely and effectively positioned within staple cartridge and/or anvil.

SUMMARY accordance with an embodiment of the present disclosure, there is provided an apparatus for joining two hollow organ sections with an annular array of surgical staples. The apparatus includes a staple cartridge component, an anvil component, a knife member, a buttress mount and a buttress member. The staple cartridge component includes a plurality of surgical staples in an annular array. The anvil component defines a plurality of staple pockets for deforming the surgical staples. The anvil component is movable relative to the staple cartridge component between spaced apart and approximated positions to adjustably clamp tissue between the staple cartridge and anvil components. The knife member is concentrically arranged with the plurality of surgical staples in the staple cartridge component. The knife member defines a lumen therethrough. The knife member is movable relative to the staple cartridge component. The buttress mount is concentrically disposed at least partially within the lumen of the knife member. The buttress mount includes a plurality of spokes radially extending outward and a plurality of legs detachably secured with an inner wall of the knife member. The buttress member is secured with the plurality of spokes of the buttress mount. The buttress member is concentrically aligned with the plurality of surgical staples.

In an embodiment, the buttress member may have an annular configuration. The buttress member may be disposed in a juxtaposed relation with the plurality of surgical staples. In addition, the plurality of spokes of the buttress mount may at least partially engage an inner portion of the buttress member. Alternatively, the plurality of spokes may engage a proximal surface the buttress member. The plurality of spokes may engage a distal surface the buttress member. The buttress member may be disposed distal of the buttress mount, as well as proximal of the plurality of spokes of the buttress mount.

The plurality of legs may each include a protrusion radially extending outward. The knife member may define a plurality of bores in an inner wall thereof. The plurality of bores may be configured and dimensioned to securely engage the protrusions of the plurality of legs therein. The buttress mount may further include an annular ring member from which the plurality of spokes radially extend outward. In particular, the annular ring member of the buttress mount may be dimensioned to receive an actuation shaft that effects axial movement of the anvil component between spaced apart and approximated positions to adjustably clamp tissue. Moreover, the annular ring member of the buttress mount may be coplanar with the buttress member. In other embodiments, the plurality of legs may be flexible. In addition, the buttress member may be made of a biodegradable material.

In accordance with another embodiment of the present disclosure, there is provided an apparatus for joining two hollow organ sections with an annular array of surgical staples. The apparatus includes a staple cartridge, an anvil component, a knife member, and a buttress member. The staple cartridge component includes a plurality of surgical staples in an annular array. The anvil component defines a plurality of staple pockets for deforming the surgical staples. The anvil component is movable relative to the staple cartridge component between spaced apart and approximated positions to adjustably clamp tissue between the staple cartridge and anvil components. The knife member is concentrically arranged with the plurality of surgical staples in the staple cartridge component. The knife member defines a lumen therethrough. The knife member is movable relative to the staple cartridge component. The buttress member includes at least a pair of anchor portions. The pair of anchor portions securely engages an inner wall of the staple cartridge component.

In an embodiment, the buttress member may be concentrically aligned with the plurality of surgical staples. In addition, the apparatus may further include an O-ring disposed within the staple cartridge component. The O-ring may apply outward force to the pair of anchor portions against the inner wall of the staple cartridge component. The staple cartridge component may define at least a pair of cavities.

In another embodiment, each of the pair of cavities may be configured and dimensioned to receive each of the pair of anchor portions. The anchor portion may include a neck portion and a head portion. The head portion may have a larger width than that of the neck portion. The pair of cavities may each include a base portion and a neck portion. The base portion of the cavity may be dimensioned to receive therethrough the head portion of the anchor portion, and the neck portion of the cavity may be dimensioned to receive the neck portion of the anchor portion. The pair of anchor portions of the buttress member may diametrically oppose each other. The pair of anchor portions of the buttress member may extend radially inward.

In accordance with still another embodiment of the present disclosure, there is provided an apparatus for joining two hollow organ sections with an annular array of surgical staples. The apparatus includes a handle assembly, an elongate tubular member, a staple cartridge component, an anvil component, a knife member, a buttress mount, and a buttress member. The handle assembly includes a firing trigger. The elongate tubular member extends distally from the handle assembly. The staple cartridge component is coupled to a distal portion of the elongate tubular member. The staple cartridge component includes a plurality of surgical staples in an annular array. The anvil component defines a plurality of staple pockets for deforming the surgical staples. The anvil component is movable relative to the staple cartridge component between spaced apart and approximated positions to clamp tissue between the staple cartridge and anvil components. The knife member is concentrically arranged with the plurality of surgical staples in the staple cartridge component. The knife member defines a lumen therethrough. The knife member is movable relative to the staple cartridge component. The buttress mount is concentrically disposed with the lumen of the knife member. The buttress mount includes a plurality of legs detachably secured with an inner wall of the lumen of the knife member. The buttress member is coupled with the plurality of legs of the buttress mount. The buttress member is concentrically aligned with the plurality of surgical staples.

The plurality of legs of the buttress mount may each include a radially extending component and a longitudinally extending component. The radially extending component may be at least partially affixed to the buttress member, and the longitudinally extending component may securely engage the lumen of the knife member.

In accordance with yet another embodiment of the present disclosure, there is provided an apparatus for joining two hollow organ sections with an annular array of surgical staples. The apparatus includes a staple cartridge component, an anvil component, a knife member and a buttress member. The staple cartridge component includes a plurality of surgical staples in an annular array. The anvil component includes an anvil plate defining a plurality of staple pockets for deforming the surgical staples and a rim disposed around a periphery of the anvil plate. The anvil component defines a circumferential gap between the anvil plate and the rim. The anvil component is movable relative to the staple cartridge component between spaced apart and approximated positions to adjustably clamp tissue between the staple cartridge and anvil components. The knife member is concentrically arranged with the plurality of surgical staples in the staple cartridge component. The knife member defines a lumen therethrough. The knife member is movable relative to the staple cartridge component. The buttress member at least partially engages the circumferential gap defined in the anvil component.

In an embodiment, the buttress member may have an annular profile. The rim of the anvil component may be configured and dimensioned to enclose a distal surface of the staple cartridge component.

In accordance with still yet another embodiment of the present disclosure, there is provided an apparatus for joining two hollow organ sections with an annular array of surgical staples. The apparatus includes staple cartridge component, an anvil component, and a buttress member. The staple cartridge component includes a distal surface. The distal surface defines an annular array of surgical staple receiving slots and a groove. The anvil component is movable relative to the staple cartridge component between spaced apart and approximated positions to adjustably clamp tissue between the staple cartridge and anvil components. The buttress member at least partially engages the groove defined the distal surface of the staple cartridge component.

The buttress member may include circumferentially arranged tabs configured and dimensioned to be received in the groove defined in the distal surface of the staple cartridge component. Moreover, the groove defined in the distal surface of the staple cartridge component may be a circumferential groove defined in a periphery of the staple cartridge component.

In an embodiment, the anvil component may include an anvil plate defining a plurality of staple pockets for deforming the surgical staples and a rim disposed around a periphery of the anvil plate. The anvil component may define a circumferential gap between the anvil plate and the rim. The apparatus may further include a second buttress member at least partially engaging the circumferential gap defined in the anvil component. The apparatus may also include a knife member concentrically arranged with the plurality of surgical staples in the staple cartridge component, wherein the knife member is movable relative to the staple cartridge component.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
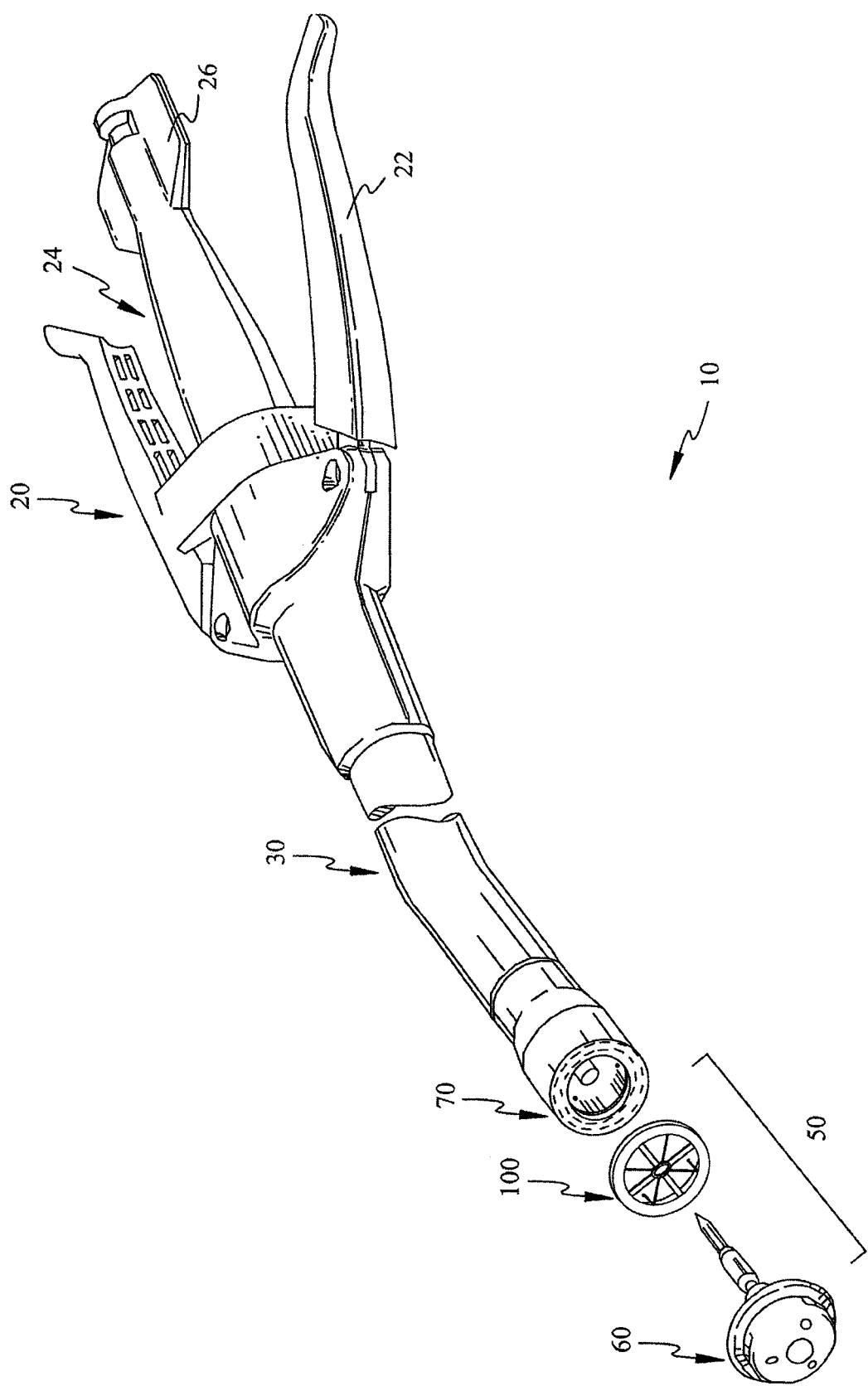
FIG. 1 is a perspective view of an annular surgical stapling apparatus configured for use with a surgical buttress assembly in accordance with an embodiment of the present disclosure illustrating an anvil assembly and the buttress assembly detached from the surgical stapling apparatus.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, a surgical stapling apparatus 10 for performing circular anastomosis of hollow organs is shown. Surgical stapling apparatus 10 drives a circular array of staples 7 (FIG. 8) through the end sections of each organ and simultaneously cores any tissue interior of the driven circular array of staples 7 to free the tubular passage, and thereby joining two ends of the organ. Surgical stapling apparatus 10 includes a handle assembly 20 having a pair of pivotable actuating handle members 22 and an advancing means 24 including a rotatable grip member 26, an elongate body portion 30 extending distally from handle assembly 20, and a head portion 50 including an anvil assembly 60, a staple cartridge assembly 70, and a surgical buttress assembly 100 in accordance with an embodiment of the present disclosure. The components of surgical apparatus 10 are generally formed from thermoplastics including polycarbonates, and metals including stainless steel and aluminum. The particular material selected to form a particular component will depend upon the strength requirements of the particular component. Staples 7 are of a conventional type and include a backspan having a pair of legs extending from the backspan. The legs terminate in tissue penetrating tips.

Handle assembly 20 can be actuated to approximate anvil assembly 60 relative to staple cartridge assembly 70 and to apply a pair of annular arrays of staples 7 through tissue. In order to properly position tissue in head portion 50, rotatable grip member 26 may be rotated to move anvil assembly 60 axially relative to staple cartridge assembly 70 between a spaced apart position and an approximated position in which anvil assembly 60 is positioned adjacent staple cartridge assembly 70 to clamp tissue therebetween. Handle members 22 may be squeezed to fire staples 7 through tissue to join two segments of tubular tissues together, as will be discussed in detail below.

Elongate body portion 30 is constructed to have a slightly curved/bent shape along its length. However, elongate body portion 30 may also be straight, as well as flexible to bend to any configuration. The length, shape and/or the diameter of elongate body portion 30 may be varied to suit a particular surgical procedure.

Figure 2:
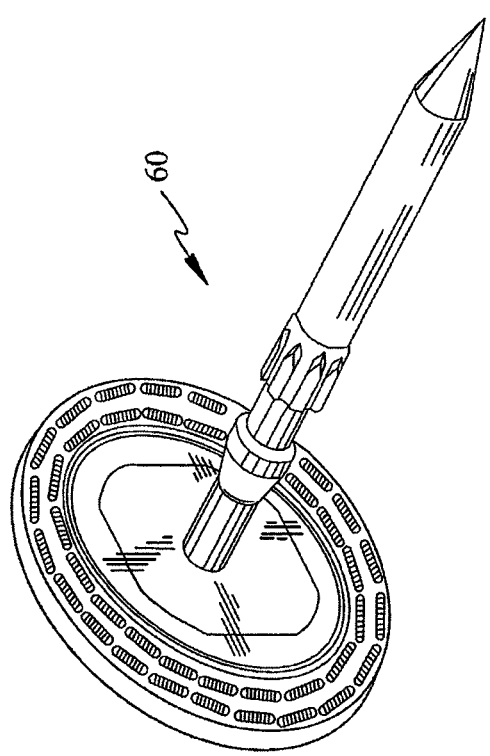
FIG. 2 is a perspective view of an anvil assembly of the surgical stapling apparatus of FIG. 1.
Figure 3:
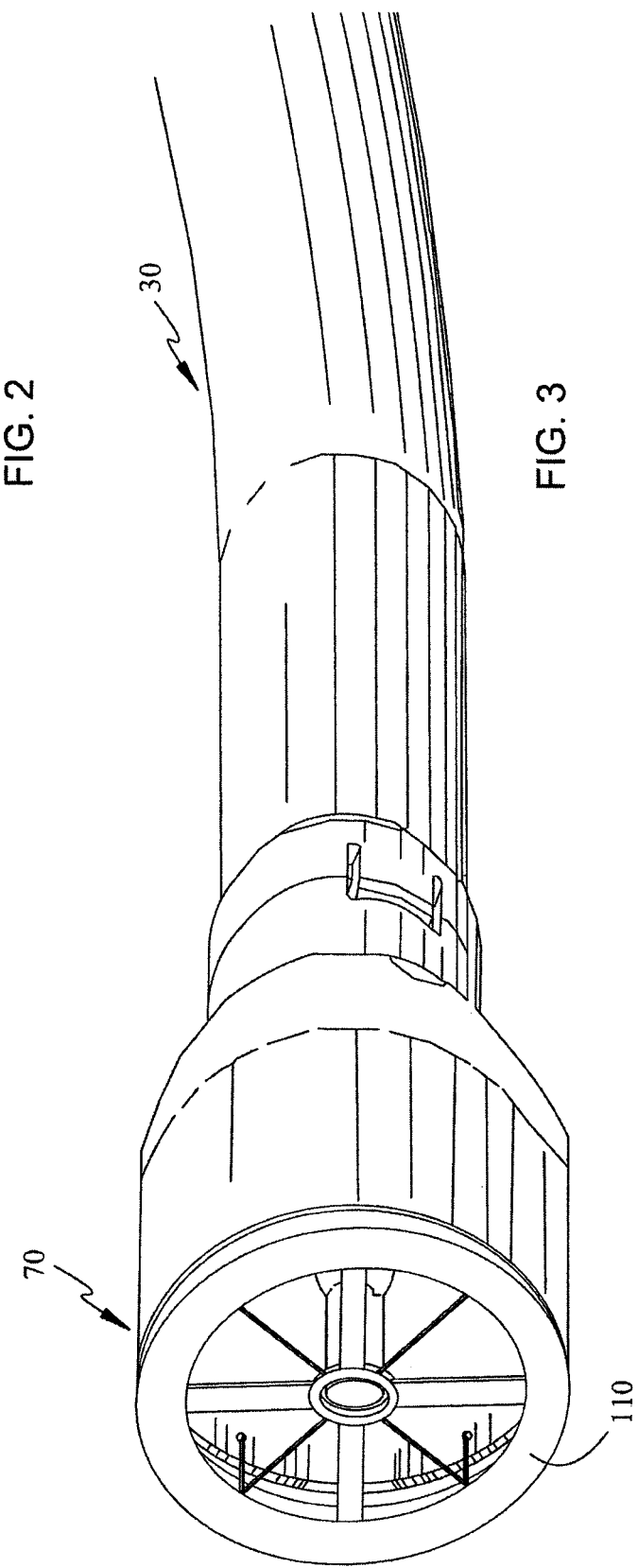
FIG. 3 is a partial perspective view of the surgical stapling apparatus of FIG. 1 illustrating a surgical buttress assembly mounted on a distal portion of the surgical stapling apparatus.
Figure 4:
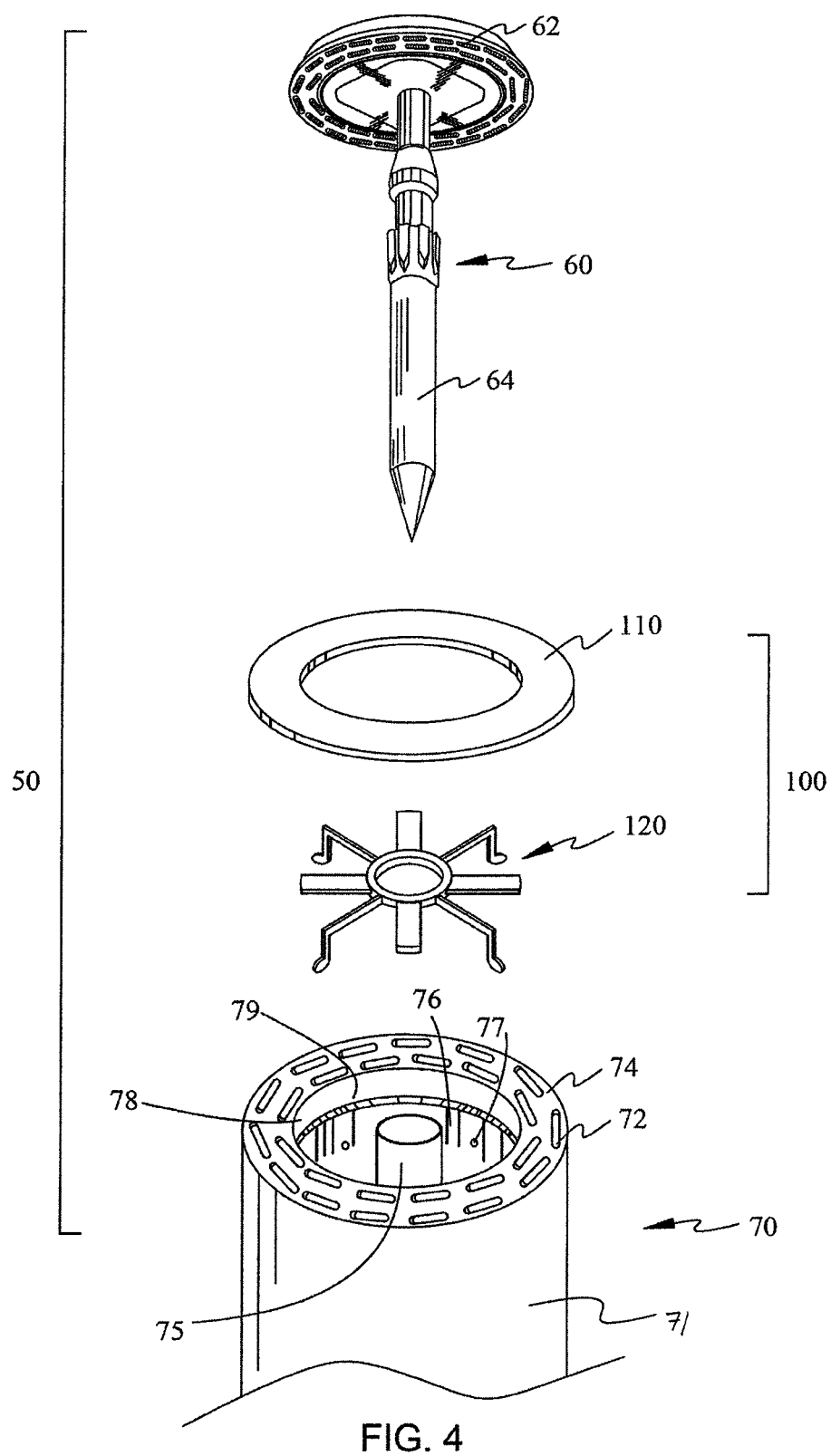
FIG. 4 is a perspective view of a head portion of the surgical stapling apparatus of FIG. 1 with parts separated.
Figure 5:
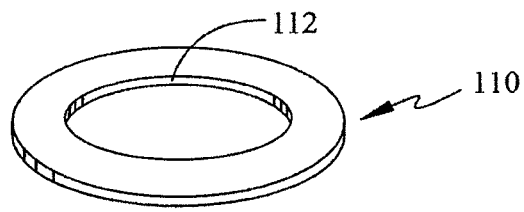
FIG. 5 is a perspective view of a buttress member of the surgical buttress assembly of FIG. 1.
Figure 6:
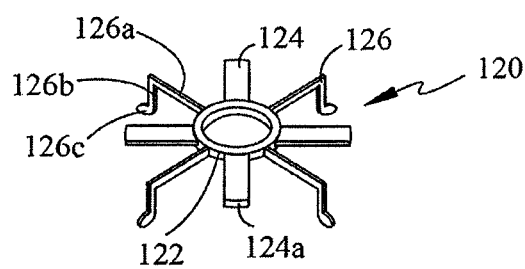
FIG. 6 is a perspective view of a buttress mount of the surgical buttress assembly of FIG. 1.
Figure 7:
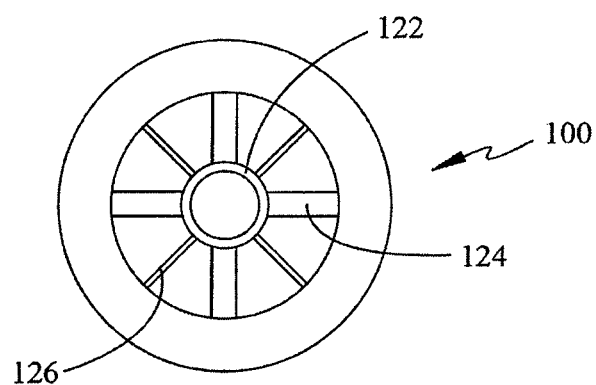
FIG. 7 is a top, plan view of the surgical buttress assembly of FIG. 1.

With reference to FIGS. 2-4, head portion 50 includes anvil assembly 60, staple cartridge assembly 70 and surgical buttress assembly 100 detachably secured with staple cartridge assembly 70. Staple cartridge assembly 70 may be fixedly connected to a distal end portion of elongate body portion 30 or may be configured to concentrically fit within the distal end portion of elongate body portion 30. In particular, staple cartridge assembly 70 defines a pair of annular arrays of staple receiving slots 72 having staple 7 disposed in each one of staple receiving slots 72. In addition, staple cartridge assembly 70 includes a cylindrical knife 76 concentrically arranged with the pair of annular array of staples 7 and a plurality of staple pushers 9 (FIG. 8) each disposed in staple receiving slot 72 to eject staple 7 through slot 72. Staples 7 travel through slots 72 and tissue toward anvil assembly 60.

With particular reference to FIG. 4, cylindrical knife 76 includes a distal rim 79 defining a knife blade adapted to cut tissue and portions of surgical buttress assembly 100. Moreover, cylindrical knife 76 defines a plurality of lateral bores 77. Each lateral bore 77 is adapted to support a portion of surgical buttress assembly 100 therein, as will be discussed in detail below. Cylindrical knife 76 is slidably mounted against inner wall 78 of staple cartridge assembly 70. Upon actuation of handle members 22, cylindrical knife 76 is moved distally to cut tissue and portions of surgical buttress assembly 100, and the plurality of pushers 9 are moved distally to eject staples 7 disposed in staple receiving slots 72 therethrough, toward anvil assembly 60.

Positioned distally of staple cartridge assembly 70 is anvil assembly 60 including an anvil member 62 and a shaft 64 extending proximally from anvil member 62. Anvil member 62 includes a plurality of pockets for receiving and deforming staples 7. Shaft 64 is configured to be detachably received in approximation shaft 75 (FIG. 4) disposed in elongate body portion 30. Approximation shaft 75 is operatively coupled with rotatable grip member 26 of handle assembly 20, whereby rotation of rotatable grip member 26 moves approximation shaft 75 axially. Such axial movement of approximation shaft 75 is imparted to anvil assembly 60 detachably coupled with approximation shaft 75. In this manner, anvil assembly 60 is movable axially relative to staple cartridge assembly 70 between a spaced apart position and an approximated position in which anvil assembly 60 is positioned adjacent staple cartridge assembly 70 to adjustably clamp tissue between anvil assembly 60 and staple cartridge assembly 70.

Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference.

With continued reference to FIG. 4, surgical buttress assembly 100 includes a buttress member 110 and a buttress mount 120 concentrically arranged with buttress member 110. Buttress member 110 is provided to reinforce and seal staple lines applied to tissue by surgical stapling apparatus 10.

Buttress member 110 has an annular profile configured to be concentrically aligned with staple cartridge assembly 70. In particular, buttress member 110 is positionable adjacent a distal surface 74 of staple cartridge assembly 70. The annular profile of buttress member 110 is configured and dimensioned to be flush with an outer peripheral edge of staple cartridge assembly 70 when supported on staple cartridge assembly 70. Moreover, buttress member 110 is superposed with the pair of annular arrays of staple receiving slots 72. In this manner, when staples 7 are ejected through the pair of annular arrays of staple receiving slots 72, the legs of each staple 7 penetrate through buttress member 110 and the backspan of the staple 7 is secured against a proximal surface of buttress member 110.

Buttress member 110 is fabricated from a biocompatible material which is bio-absorbable or non-absorbable, as well as natural or synthetic materials. It should be understood that any combination of natural, synthetic, bio-absorbable, and non-bioabsorbable materials may be used to form buttress member 110.

In addition, buttress member 110 may be porous, non-porous, or combinations thereof. It is also envisioned that buttress member 110 described herein may contain a plurality of layers in which any combination of non-porous and porous layers may be configured. For example, buttress member 110 may be formed to include multiple non-porous layers and porous layers that are stacked in an alternating manner. In another example, buttress member 110 may be formed in a "sandwich-like" manner wherein the outer layers of buttress member 110 include porous layers and the inner layers are non-porous layers. Examples of multi-layered buttress members are disclosed in U.S. Patent Application Publication No. 2009/0001122, filed on Jun. 27, 2007, entitled "Buttress and Surgical Stapling Apparatus," the entire disclosure of which is incorporated by reference therein.

In particular, the use of non-porous layers in buttress member 110 may enhance the ability of buttress member 110 to resist tears and perforations during the manufacturing, shipping, handling, and stapling processes. In addition, the use of a non-porous layer in the surgical buttress may also retard or inhibit tissue ingrowth from surrounding tissues, and thereby acting as an adhesion barrier and inhibiting the formation of unwanted scar tissue.

In addition, at least one bioactive agent may be combined with buttress member 110. The agent may be disposed on a surface of the surgical buttress and/or impregnated therein. In these embodiments, buttress member 110 can also serve as a vehicle for delivery of the bioactive agent. The term "bioactive agent," as used herein, is used in its broadest sense and includes any substance or mixture of substances that have clinical use.

With reference now to FIGS. 5-8, buttress member 110 is detachably positioned adjacent surface 74 (FIG. 4) of staple cartridge assembly 70 by buttress mount 120. Buttress mount 120 includes a core ring 122, support arms 124 radially extending outward from core ring 122, and mount legs 126 also radially extending outward from core ring 122. Support arms 124 are circumferentially arranged about core ring 122. Support arms 124 are configured and dimensioned to be affixed to an inner wall 112 of buttress member 110 or to a lower surface of buttress member 110. In particular, distal end portions 124a of support arms 124 are affixed to buttress member 110 by, for example, adhesive, ultrasonic welding, or the like.

Mount legs 126 are circumferentially arranged about core ring 122, such that each mount leg 126 is interposed between a pair of adjacent support arms 124. Each mount leg 126 includes a radially extending component 126a and a longitudinally extending component 126b. Each longitudinally extending component 126b includes a protrusion 126c that is dimensioned and adapted to securely engage lateral bore 77 defined in cylindrical knife 76. Securement of protrusions 126c in lateral bores 77 of cylindrical knife 76 enables detachable mounting of buttress assembly 100 on staple cartridge assembly 70. In particular, mount legs 126 may be made of flexible or elastic material to enable flexing of mount legs 126, whereby a user may simply, for example, squeeze mount legs 126 radially inward, to attach or detach buttress assembly 100 to and from cylindrical knife 76. It is further contemplated that while core ring 122, support arm 124 and mount legs 126 have been described as individually manufactured components, such components may be monolithically formed as a single construct.

Figure 8:
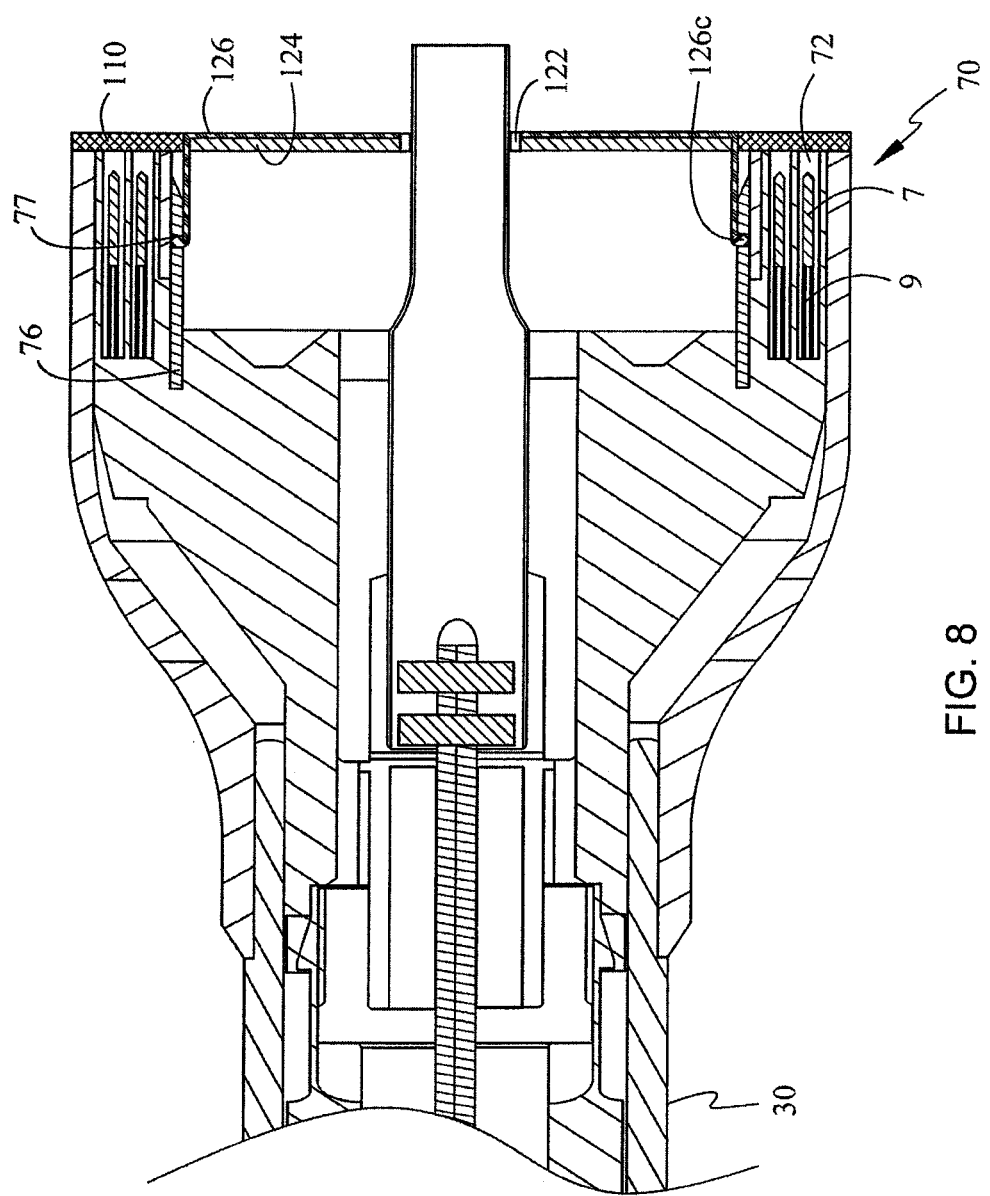
FIG. 8 is a longitudinal cross-sectional view of a distal end portion of the surgical stapling apparatus of FIG. 1.

With particular reference now to FIG. 8, buttress member 110 is superposed with staple receiving slots 72 defined in distal surface 74 of staple cartridge assembly 70 and is coupled with core ring 122 by support arm 124. Core ring 122 is also coupled to mount legs 126, as described above. Protrusions 126c of mount legs 126 securely engage lateral bores 77 defined in cylindrical knife 76, which is disposed radially inward of annular array of staple receiving slots 72. In this manner, upon actuation of handle members 22, a portion of buttress member 110 is stapled with tissue to reinforce tissue, and the remaining portions of buttress member 110 and buttress mount 120 are cut and detached from the portion of buttress member 110 stapled with tissue.

Figure 9:
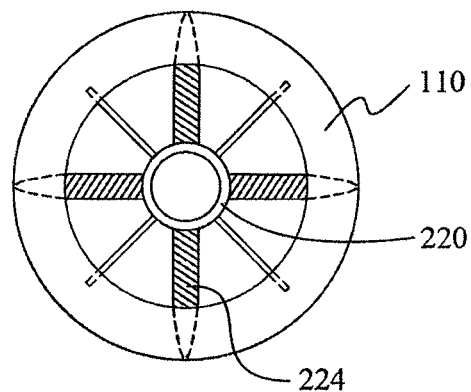
FIG. 9 is a top, plan view of an embodiment of a surgical buttress assembly for use with the surgical stapling apparatus of FIG. 1.

With reference to FIG. 9, in another embodiment, it is further envisioned that buttress mount 220 need not be substantially coplanar with buttress member 110, as shown in, for example, FIG. 4. Rather, support arms 224 may be disposed proximal of buttress member 110 to provide a more secure contact between support arm 224 of buttress mount 220 and buttress member 110 (by providing a greater area of contact), whereby an outer edge portion of support arm 224 (shown in phantom) is affixed to buttress member 110 by, for example, adhesive or ultrasonic welding or the like.

Figure 10:
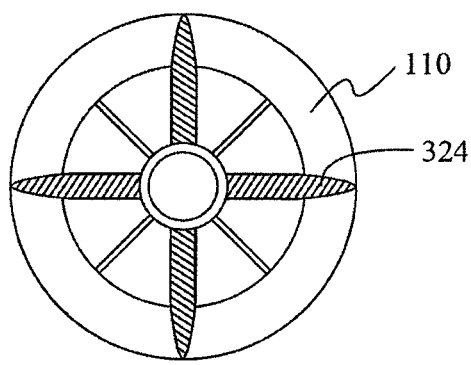
FIG. 10 is a top, plan view of another embodiment of a surgical buttress assembly for use with the surgical stapling apparatus of FIG. 1.
Figure 11:
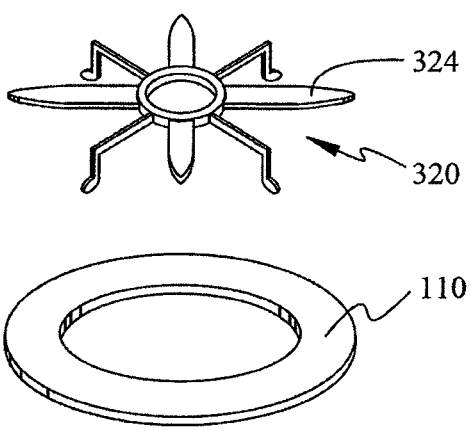
FIG. 11 is a perspective view of the surgical buttress assembly of FIG. 10 with the buttress member and the buttress mount separated.

With reference now to FIGS. 10 and 11, support arms 324 of another embodiment of a buttress mount 320 may be disposed distal of buttress member 110, and thereby providing a more secure mounting of buttress member 110 on staple cartridge assembly 70. Support arms 324 aid in pressing buttress member 110 against distal surface 74 of staple cartridge assembly 70. Under such configurations, it is contemplated that at least the outer edge portions of support arms 324 that are stapled to tissue are fabricated from a bio-absorbable material.

Figure 12:
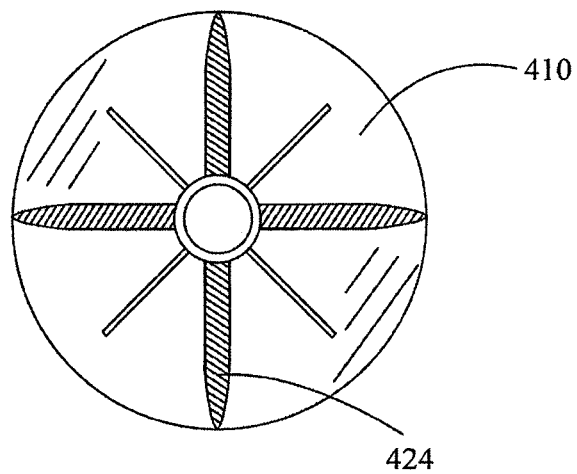
FIG. 12 is a top, plan view of another embodiment of a surgical buttress assembly for use with the surgical stapling apparatus of FIG. 1.

With reference to FIG. 12, it is further envisioned that a buttress member 410 may have a circular cross-section to improve mounting of buttress member 410 on distal surface 74 of staple cartridge assembly 70. By providing a greater contact area between buttress member 410 and support arms 424, the force applied to buttress member 410 by support arm 424 is more evenly distributed throughout buttress member 410, which may inhibit tear or damage to buttress member 410. While support arms 424, as shown, are positioned distal of buttress member 410, it is also envisioned that support arms 424 may be positioned proximal of buttress member 410.

Figure 13:
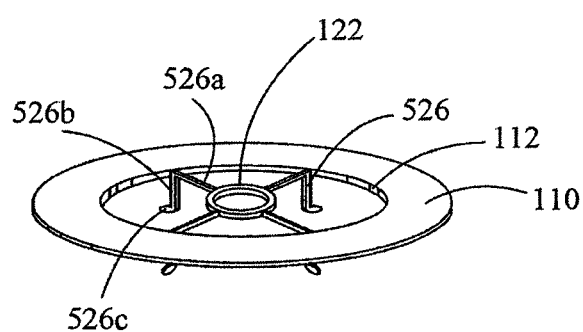
FIG. 13 is a perspective view of still another embodiment of a surgical buttress assembly for use with the surgical stapling apparatus of FIG. 1.
Figure 14:
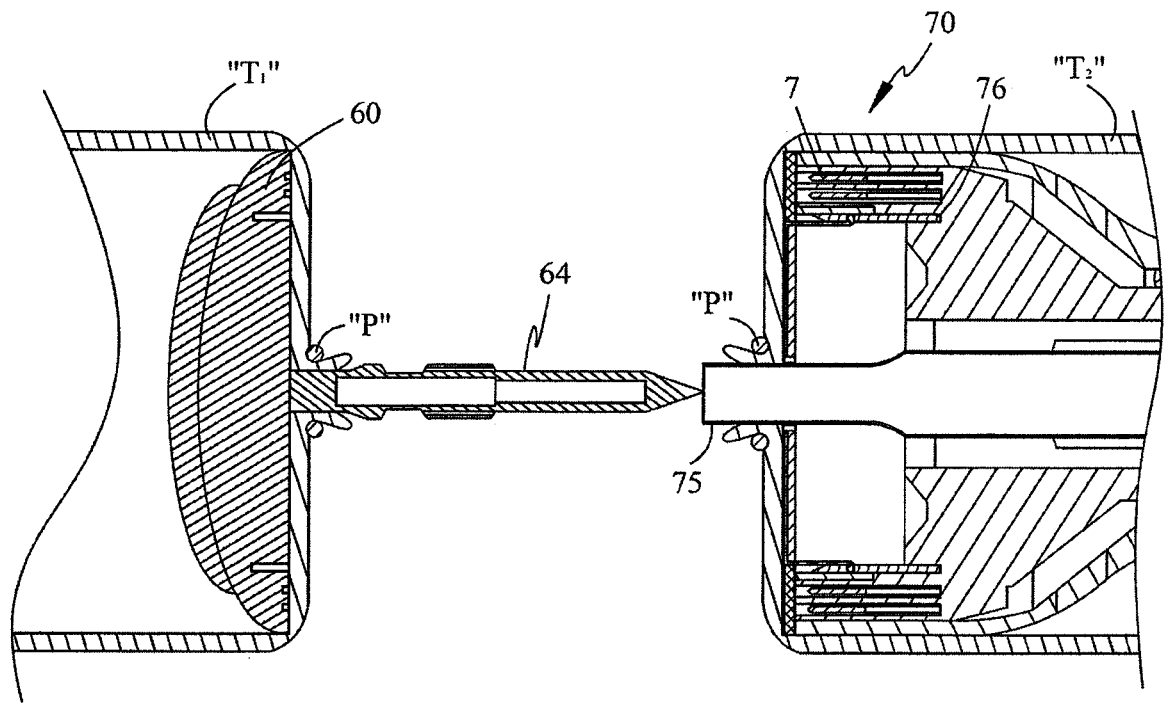
FIGS. 14-17 are longitudinal cross-sectional views of a distal end portion of the surgical stapling apparatus of FIG. 1 illustrating a method of use therefor.

With reference to FIG. 13, it is further envisioned that buttress mount assembly 100 may be simplified by having buttress member 110 coupled to core ring 122 by mount legs 526. Specifically, mount legs 526 are utilized to couple buttress member 110 to core ring 122, and to detachably engage lateral bores 77 defined in cylindrical knife 76. In particular, each mount leg 526 includes a radially extending component 526a, a longitudinally extending component 526b, and a protrusion 526c dimensioned and adapted to securely engage lateral bores 77 in cylindrical knife 76. According to the present disclosure, longitudinally extending component 526b is attached to inner wall 112 of buttress member 110. However, longitudinally extending components 526b of mount legs 526 may be radially flexible to enable a user to detachably secure buttress 110 to cylindrical knife 76 (as described hereinabove with respect to mount legs 126).

With reference to FIGS. 14-17, surgical stapling apparatus 10 is used in an anastomosis procedure to effect joining of, for example, two opposing intestinal sections "$T_1$, $T_2$." The anastomosis procedure is typically performed using minimally invasive surgical techniques including laparoscopic means and instrumentation. Initially, a diseased intestinal section is removed. Thereafter, anvil assembly 60 is inserted to the operative site either through a surgical incision or transanally and is positioned within the intestinal section "$T_1$." Elongate body portion 30 of surgical stapling apparatus 10 including staple cartridge assembly 70 is inserted transanally into the other intestinal section "$T_2$." The intestinal sections "$T_1$, $T_2$" are then temporarily secured about their respective components (e.g., shaft 64 of anvil assembly 60 and the distal end of elongate body portion 30) by conventional means such as a purse string suture "P."

Figure 15:
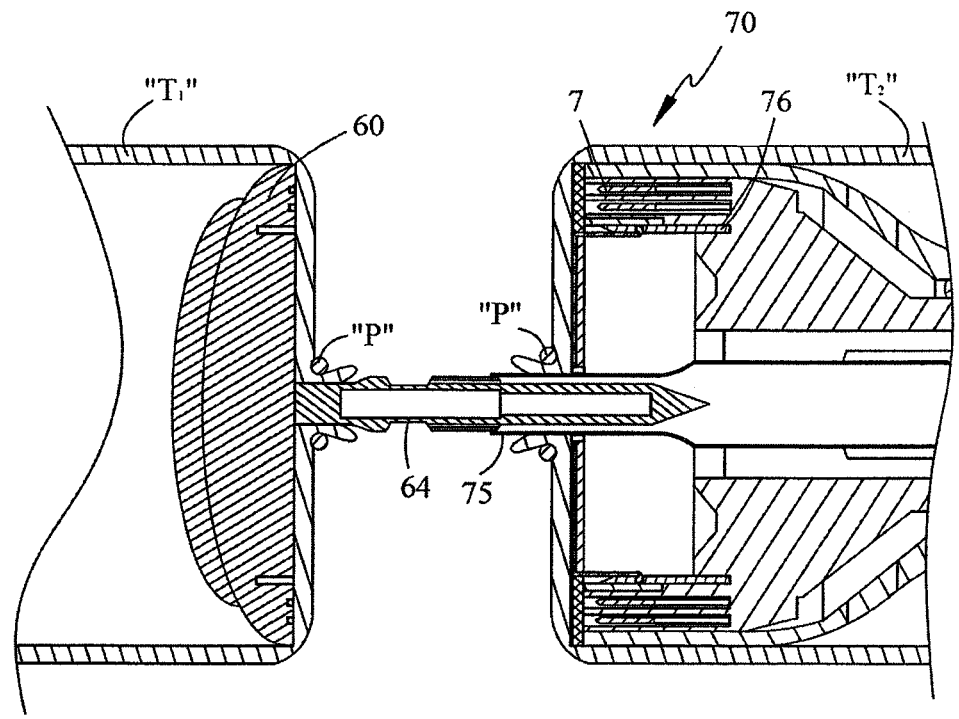
Figure 16:
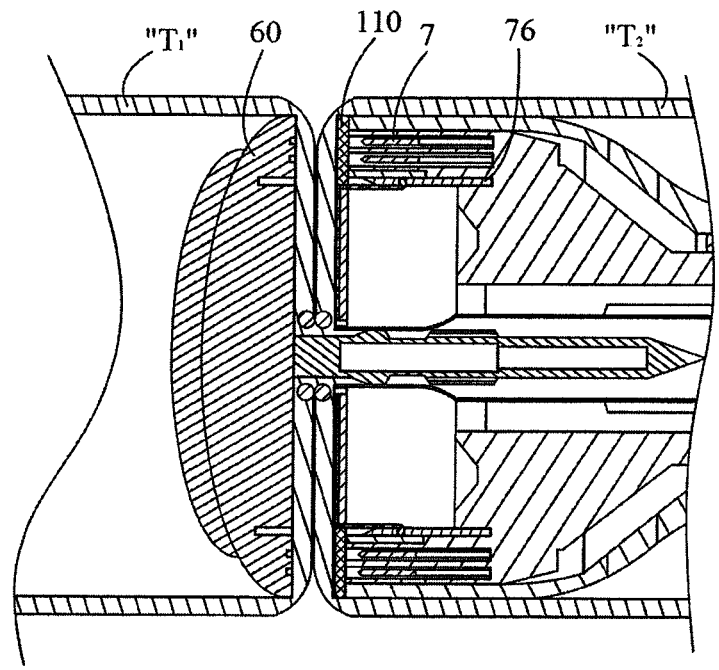
Figure 17:
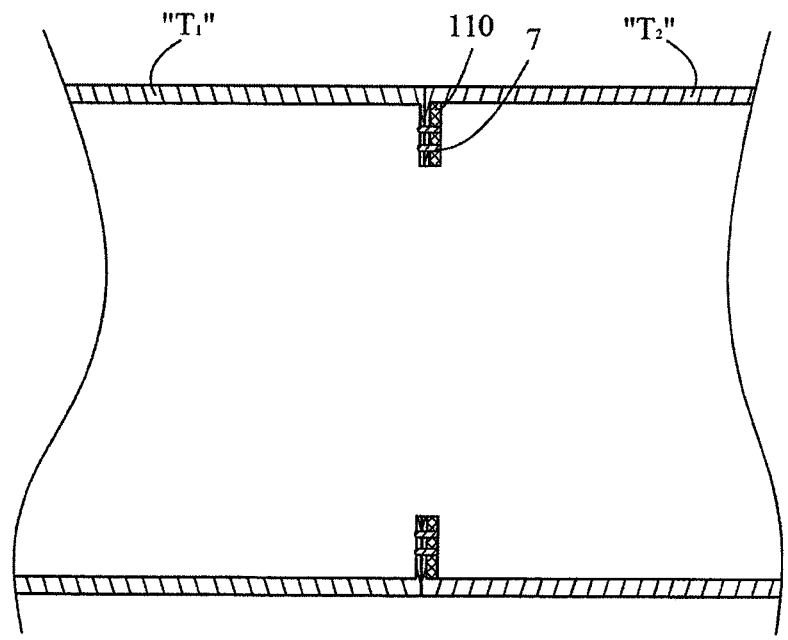

Thereafter, the clinician maneuvers anvil assembly 60 until the proximal end of shaft 64 is inserted into the distal end of approximation shaft 75 disposed in elongate body portion 30 of surgical stapling apparatus 10. Shaft 64 engages approximation shaft 75 to be operable as a unitary construct, as shown in FIG. 15. Anvil assembly 60 and elongate body portion 30 are then approximated to approximate the intestinal sections "$T_1$, $T_2$," as shown in FIG. 16. Surgical stapling apparatus 10 is then fired, effecting stapling of the intestinal sections "$T_1$, $T_2$" to one another, while cylindrical knife 76 cuts a portion of buttress member 110 and tissue disposed interior of cylindrical knife 76, and thereby detaching buttress mount 120 and an inner portion of buttress member 110 from the portion of buttress member 110 that is clamped (approximated) between distal surface 74 of staple cartridge assembly 70 and anvil assembly 60 to complete the anastomosis.

Figure 18:
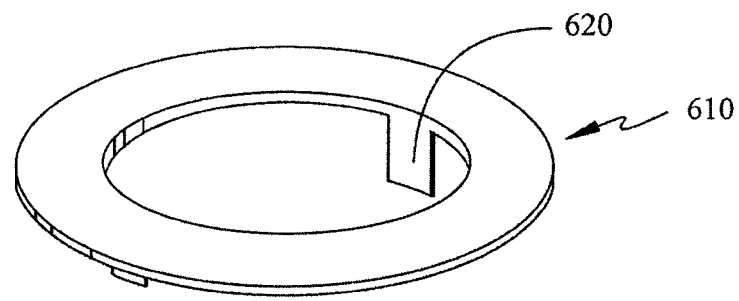
FIG. 18 is a perspective view of a buttress member in accordance with another embodiment of the present disclosure.
Figure 19:
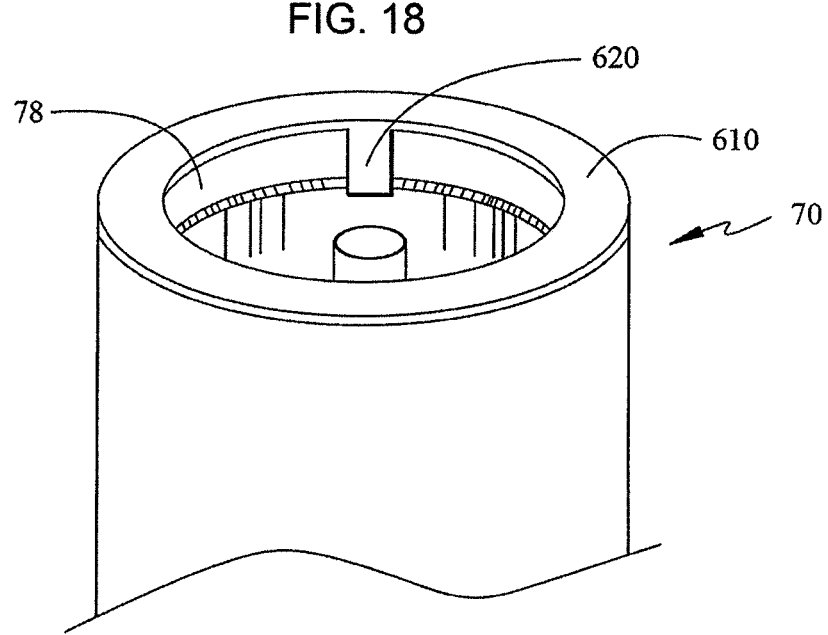
FIG. 19 is a perspective view of a surgical cartridge assembly of FIG. 1 having the buttress member of FIG. 18 mounted thereon.

With reference to FIG. 18, a buttress member 610 in accordance with another embodiment of the present disclosure is illustrated. In contrast to the above-described buttress member 110, buttress member 610 simplifies a buttress assembly by eliminating the need for buttress mount 120. Buttress member 610 is substantially similar to buttress member 110. However, buttress member 610 includes a plurality of longitudinally extending tabs 620 circumferentially arranged about buttress member 610. Longitudinally extending tabs 620 slightly extend radially outward, such that when buttress member 610 is disposed on distal surface 74 of staple cartridge assembly 70 and is superposed with the pair of annular array of staple receiving slots 72, tabs 620 press or apply outward force against inner wall 78 of staple cartridge assembly 70. Such configuration enables buttress member 610 to be securely positioned in place with respect to staple cartridge assembly 70.

Figure 20:
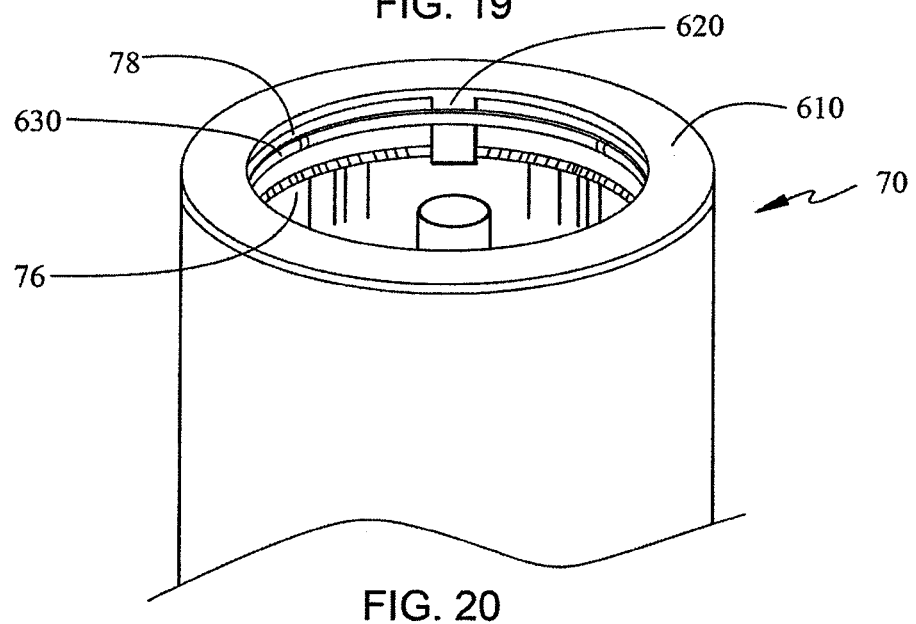
FIG. 20 is a perspective view of the buttress member of FIG. 18 mounted on the surgical cartridge assembly of FIG. 19 illustrating its use with an O-ring.

With reference to FIG. 20, it is further contemplated that a resilient O-ring 630 may be utilized with buttress member 610. O-ring 630 further applies outward force against tabs 620, which press against inner wall 78 of staple cartridge assembly 70.

Figure 21:
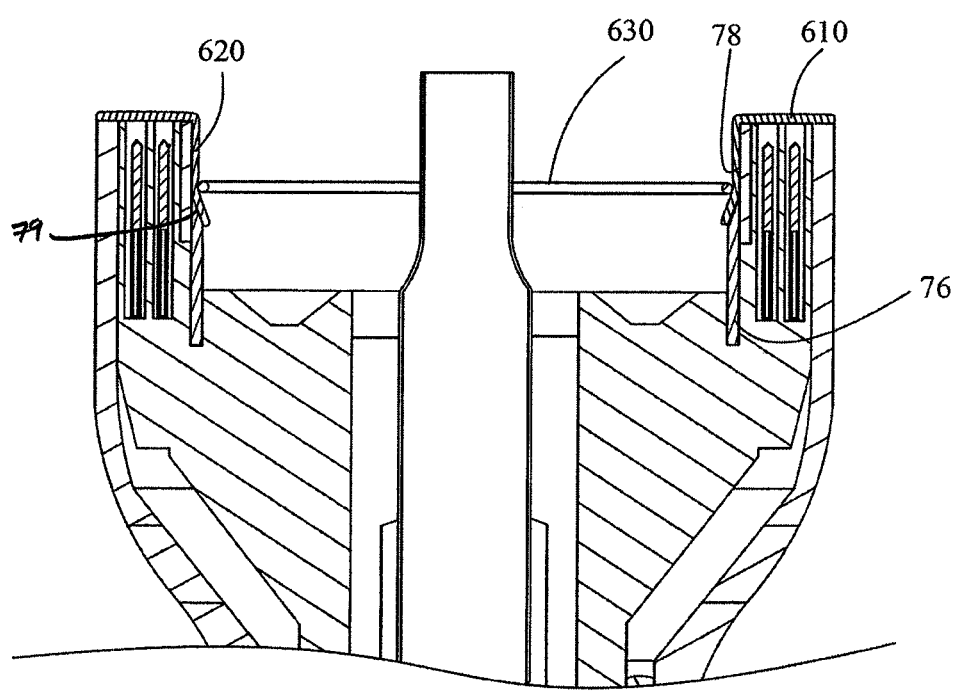
FIG. 21 is a longitudinal cross-sectional view of the surgical cartridge assembly of FIG. 20 having the buttress member of FIG. 18 mounted thereon.

With reference to FIG. 21, prior to the actuation of cylindrical knife 76, distal portions of tabs 620 of buttress member 610 are at least partially disposed on distal rim 79 of cylindrical knife 76 defining a knife blade. Under such configuration, when cylindrical knife 76 is actuated, knife 76 travels distally between inner wall 78 of staple cartridge assembly 70 and tabs 620 to cut tabs 620 from a portion of buttress member 610 that is attached with tissue. Moreover, in order to improve securement of the distal portions of tabs 620 against inner wall 78 and on distal rim 79 of cylindrical knife 76, resilient O-ring 630 is utilized and is positioned distal of distal rim 79 of cylindrical knife 76. The use and operation of buttress member 610 is substantially similar to the use and operation of buttress member 110 described hereinabove, and thus will not be described herein.

Figure 22:
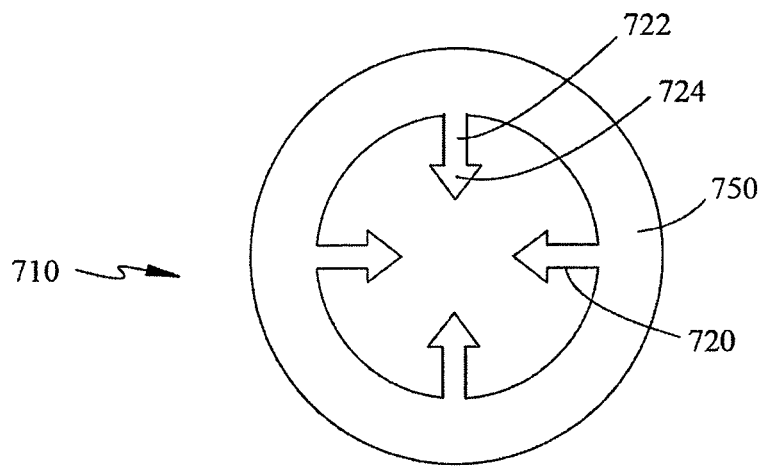
FIGS. 22-24 are top, plan views of various embodiments of buttress members.
Figure 23:
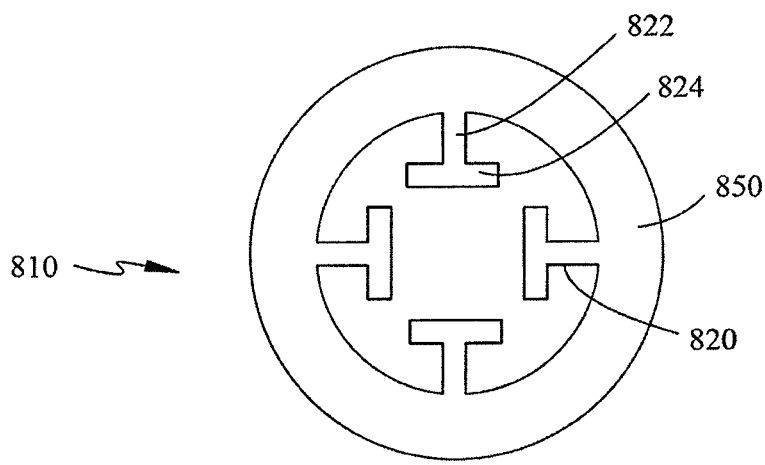
Figure 24:
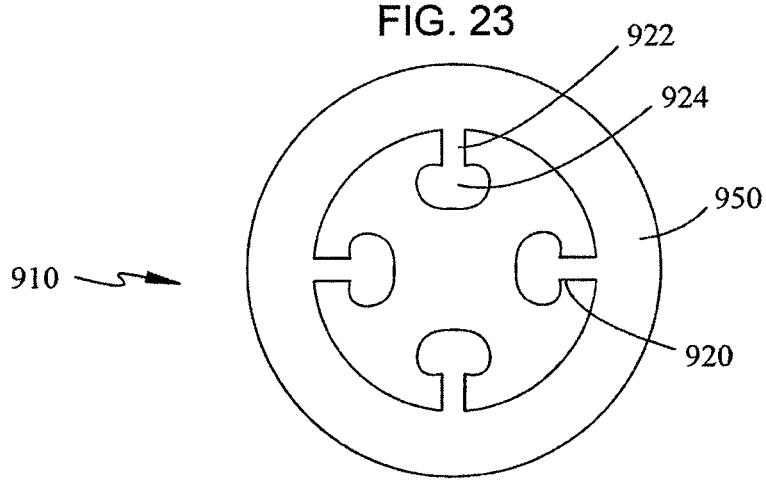

With reference to FIGS. 22-24, it is further contemplated that buttress members 710, 810, 910 may include two pairs of diametrically opposing tabs 720, 820, 920, respectively, having various shapes and profiles. Each tab 720, 820, 920 includes a respective neck portion 722, 822, 922 extending radially inward from respective annular shaped portions 750, 850, 950 of respective buttress members 710, 810, 910 and a respective head portion 724, 824, 924 having a width larger than that of respective neck portions 722, 822, 922.

Figure 25:
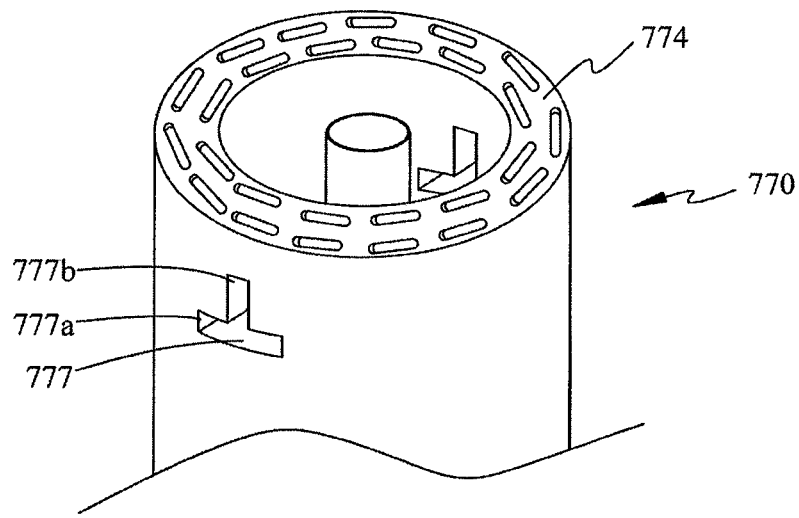
FIG. 25 is a perspective view of a surgical cartridge assembly configured for use with the buttress members of FIGS. 22-24.

With reference to FIG. 25, it is contemplated that a staple cartridge assembly 770 may define cavities 777 in lateral wall thereof to receive respective tabs 720, 820, 920 of respective buttress member 710, 810, 910 having various shapes and cross-sections. Each cavity 777 is adapted to receive tabs 720, 820, 920 of a respective buttress member 710, 810, 910 having various shapes and cross-sections. In particular, each cavity 777 has a T-shaped cross-section including a base portion 777a and a neck portion 777b having a smaller width than that of base portion 777a.

Each head portion 724, 824, 924 of respective buttress member 710, 810, 910 is configured to be received through base portion 777a of staple cartridge assembly 770 such that head portion 724, 824, 924 is disposed radially outward of base portion 777a of cavity 777. Neck portions 722, 822, 922 of respective tabs 720, 820, 920 are configured and dimensioned to be inserted through neck portion 777b of cavity 777.

It is contemplated that each tab 720, 820, 920 may be made of an elastic material to enable flexible stretching of tab 720. Thus, when head portions 724, 824, 924 of respective tabs 720, 820, 920 are securely anchored to neck portions 777b of cavities 777, neck portions 722, 822, 922 of respective tabs 720, 820, 920 are stretched to facilitate secure engagement of respective buttress member 710, 810, 910 with distal surface 774 of staple cartridge assembly 770.

Figure 26:
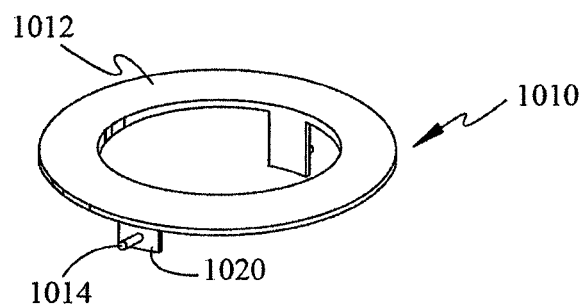
FIG. 26 is a perspective view of another embodiment of a buttress member for use with the surgical stapling apparatus of FIG. 1.
Figure 27:
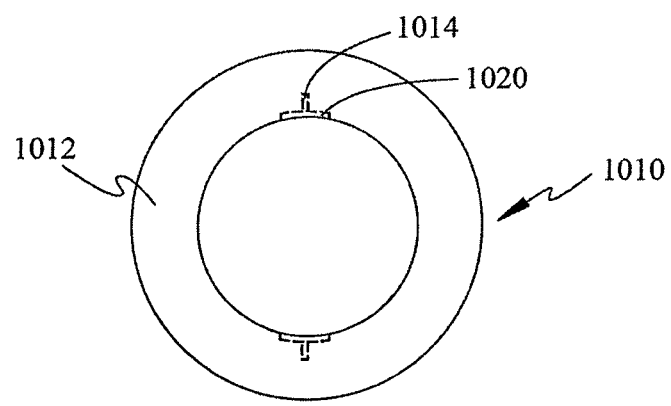
FIG. 27 is a top, plan view of the buttress member of FIG. 26.

With reference to FIGS. 26 and 27, a buttress member 1010 in accordance with another embodiment of the present disclosure includes tabs 1020 configured to be detachably secured to cylindrical knife 76 of staple cartridge assembly 70. In particular, buttress member 1010 includes an annular shaped portion 1012 and a pair of diametrically opposing tabs 1020. Each tab 1020 includes a peg or a pin 1014 extending radially outward. Each peg 1014 is configured and dimensioned to be received in lateral bore 77 of cylindrical knife 76 of staple cartridge assembly 70. Under such configuration, buttress member 1010 is securely mounted on staple cartridge assembly 70 without having to use a buttress mount.

Figure 28:
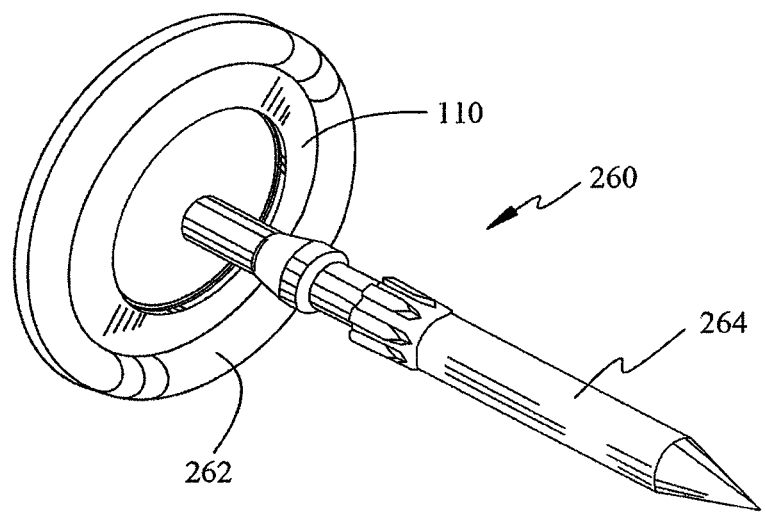
FIG. 28 is a perspective view of an anvil assembly configured for use with the buttress member of the buttress assembly of FIG. 1.
Figure 29:
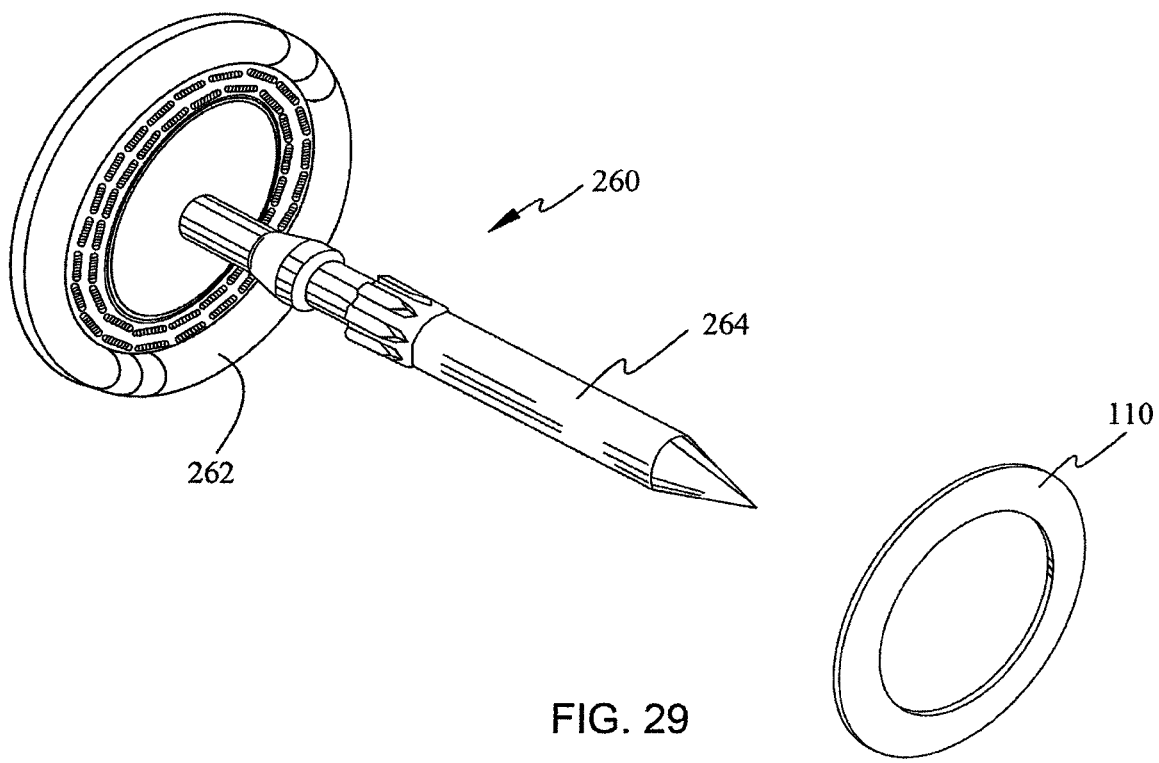
FIG. 29 is a perspective view of the anvil assembly of FIG. 28 with the buttress member separated therefrom.

Buttress member 110 described hereinabove has utilized staple cartridge assembly 70 as a way to be secured with surgical stapling apparatus 10. However, with reference to FIGS. 28-30, buttress member 110 may be mounted on an anvil assembly 260. Similar to anvil assembly 60, anvil assembly 260 includes anvil member 262 defining a plurality of pockets against which legs of staple 7 are deformed and a shaft 264 extending from anvil member 262.

Figure 30:
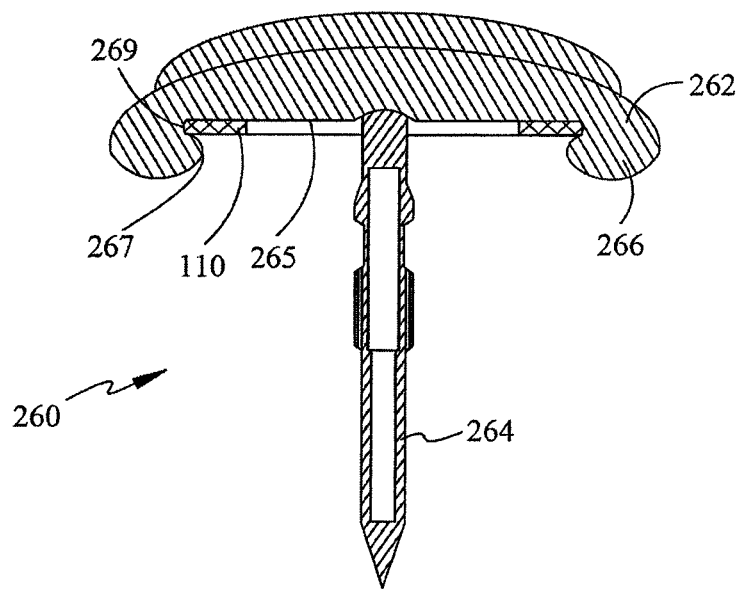
FIG. 30 is a longitudinal cross-sectional view of the anvil assembly of FIG. 28.

With particular reference to FIG. 30, anvil member 262 includes a rim 266 defining an arcuate portion 267. Arcuate portion 267 engages an outer wall 71 (FIG. 4) of staple cartridge assembly 70, whereby anvil member 262 encloses distal surface 74 of staple cartridge assembly 70. In particular, a gap 269 is defined between arcuate portion 267 and an underside 265 of anvil member 262, such that buttress member 110 is at least partially wedged and securely supported within gap 269. In this manner, buttress member 110 is securely mounted on anvil assembly 260 without having to utilize a buttress mount.

Figure 31:
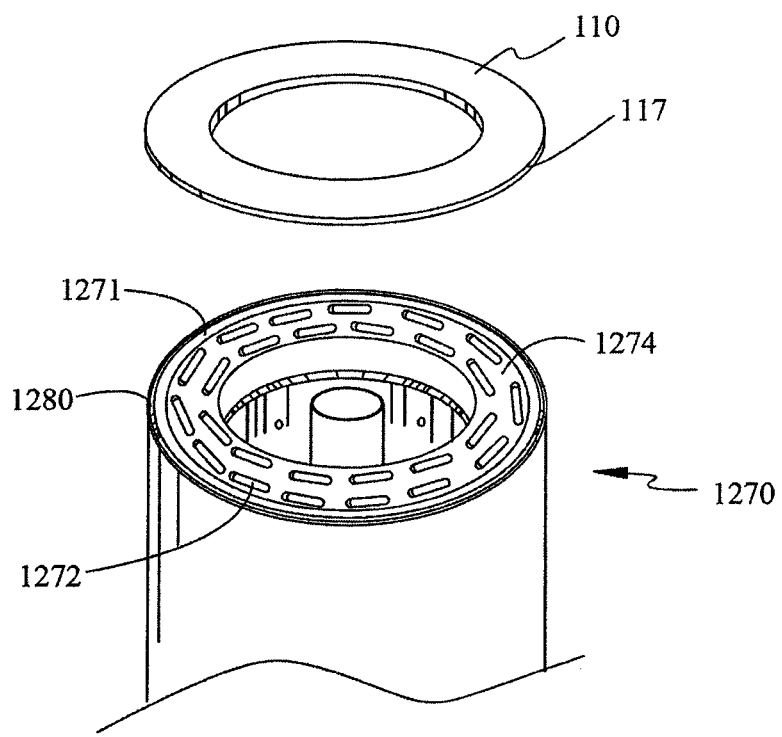
FIG. 31 is a perspective view of a staple cartridge assembly configured to directly mount the buttress member of FIG. 1 thereon illustrating the buttress member separated therefrom.
Figure 32:
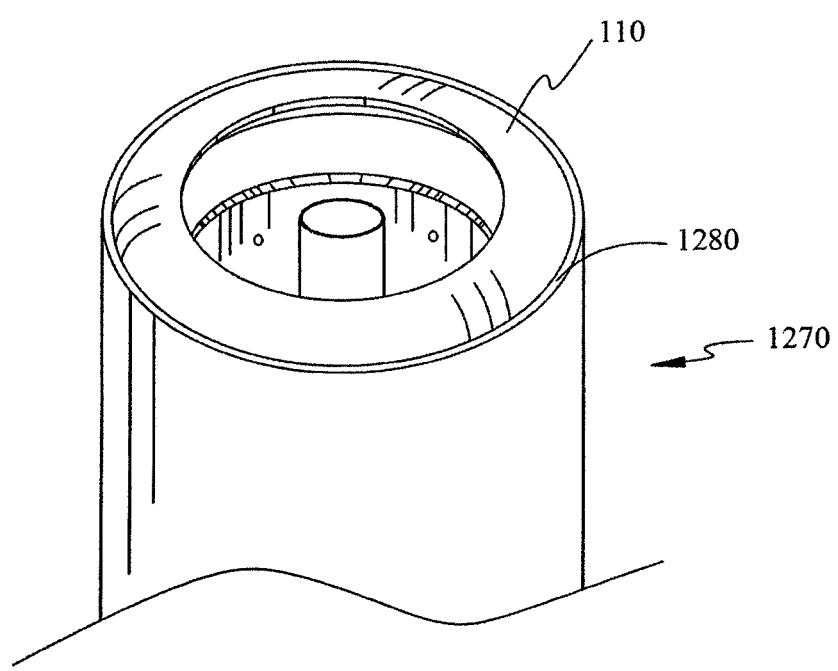
FIG. 32 is a perspective view of the staple cartridge assembly of FIG. 31 having the buttress member of FIG. 1 directly mounted thereon.
Figure 33:
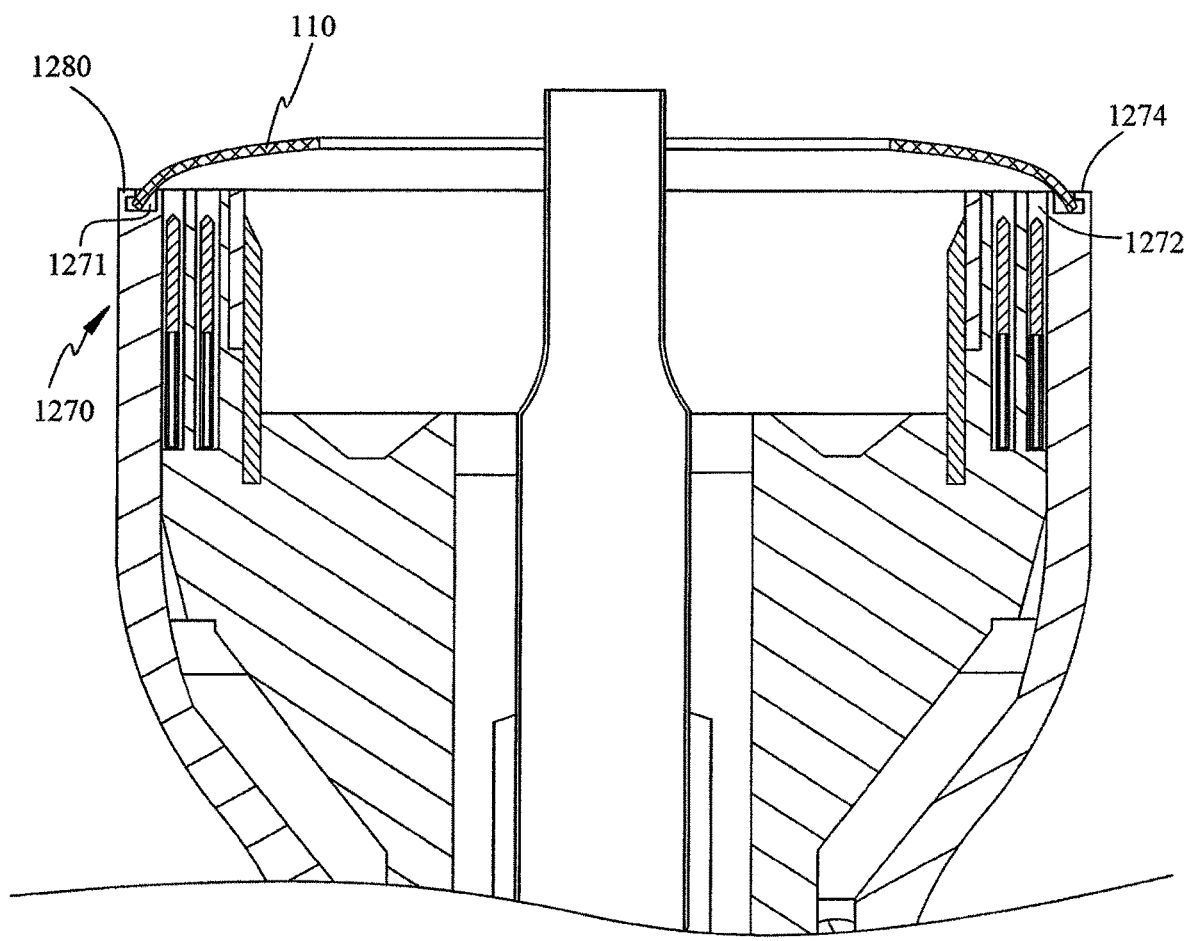
FIG. 33 is a longitudinal cross-sectional view of the staple cartridge assembly of FIG. 32 having the buttress member of FIG. 1 directly mounted thereon.

With reference now to FIGS. 31-33, a staple cartridge assembly 1270 defines a circumferential groove 1271 concentrically arranged with a pair of annular arrays of staple receiving slots 1272. Distal surface 1274 of staple cartridge assembly 1270 includes an overhang 1280 that partially covers groove 1271, whereby when a peripheral portion 117 of buttress member 110 is disposed in groove 1271, overhang 1280 ensures that peripheral portion 117 of buttress member 110 is securely retained in groove 1271. In this manner, buttress member 110 is directly mounted on staple cartridge assembly 1270 without having to utilize buttress mount 120.

Figure 34:
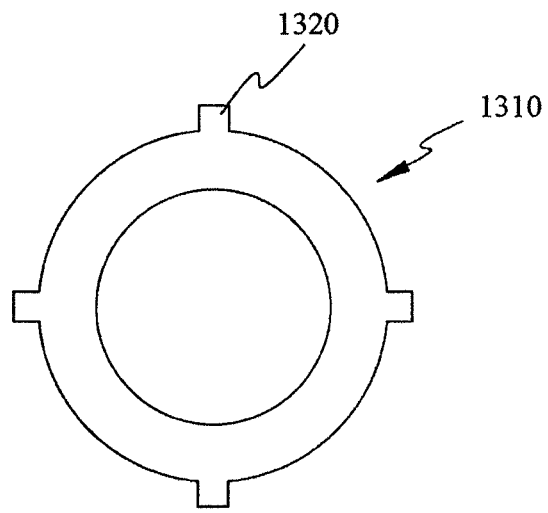
FIG. 34 is a top, plan view of another embodiment of a buttress member for use with the stapling cartridge assembly of FIG. 31.
Figure 35:
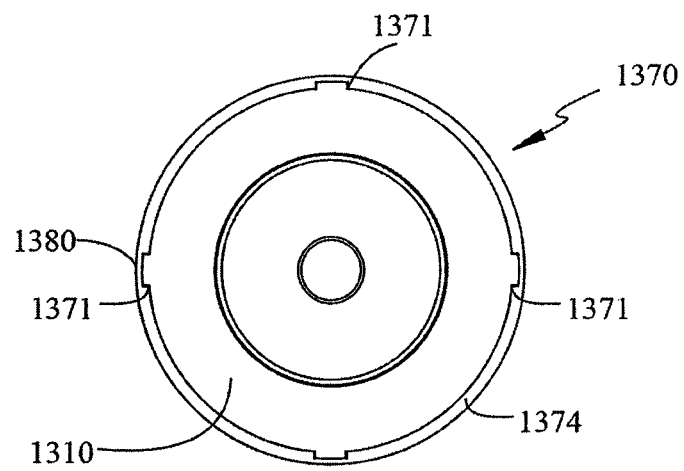
FIG. 35 is a top, plan view of another embodiment of a staple cartridge assembly configured for use with the buttress member of FIG. 34.

With reference to FIGS. 34 and 35, it is also envisioned that a staple cartridge assembly 1370 may define discrete grooves 1371 on a distal surface 1374 therein. Discrete grooves 1371 are circumferentially arranged about staple cartridge assembly 1370. Each groove 1371 may be configured and dimensioned to receive therein a portion of a buttress member 1310. Buttress member 1310 is substantially similar to buttress members described hereinabove. Buttress member 1310, however, includes tabs 1320 that radially extend outward. Each tab 1320 is configured and dimensioned to be disposed in a respective groove 1371 of staple cartridge assembly 1370. As discussed hereinabove, each groove 1371 may be at least partially covered by an overhang 1380, whereby when tabs 1320 of buttress member 1310 are disposed in grooves 1371 overhang 1380 ensures that tabs 1320 are securely retained in groove 1371.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An apparatus for joining two hollow organ sections with an annular array of surgical staples, the apparatus comprising:

a staple cartridge component including a distal surface and an overhang extending distally from the distal surface, the distal surface defining an annular array of surgical staple receiving slots and circumferentially arranged grooves extending proximally from the distal surface, the circumferentially arranged grooves being separate from each other, the overhang in partial registration with one of the circumferentially arranged grooves;

an anvil component movable relative to the staple cartridge component between spaced apart and approximated positions to adjustably clamp tissue between the staple cartridge and anvil components; and a buttress member including circumferentially arranged tabs configured to be received in the respective circumferentially arranged grooves of the staple cartridge component, at least a portion of one of the circumferentially arranged tabs in registration with the overhang of the staple cartridge component such that the at least a portion of one of the circumferentially arranged tabs is interposed between the overhang and the distal surface of the staple cartridge component, wherein the circumferentially arranged grooves of the distal surface of the staple cartridge component are fixed irrespective of placement of the circumferentially arranged tabs of the buttress member therein, at least a portion of one of the circumferentially arranged tabs being disposed proximal of the distal surface of the staple cartridge component.

2. The apparatus according to claim 1, wherein the circumferentially arranged grooves are defined in a peripheral portion of the staple cartridge component.

3. The apparatus according to claim 1, further comprising a knife member concentrically arranged with the annular array of surgical staples in the staple cartridge component, the knife member movable relative to the staple cartridge component.

4. The apparatus according to claim 1, wherein the distal surface and the overhang of the staple cartridge component are formed as a single construct.

5. The apparatus according to claim 4, wherein at least a portion of the overhang of the staple cartridge component is distal of the buttress member.

6. An apparatus for joining two hollow organ sections with an annular array of surgical staples, the apparatus comprising:
  a staple cartridge component including a distal surface defining an annular array of surgical staple receiving slots and a stationary groove extending radially outward and proximally from the distal surface, the stationary groove defined inwardly of an outer periphery of the staple cartridge component, the distal surface including a stationary overhang in partial registration with the stationary groove;
  an anvil component movable relative to the staple cartridge component between spaced apart and approximated positions to adjustably clamp tissue between the staple cartridge and anvil components; and
  a buttress member configured to be received in the stationary groove of the staple cartridge component, the stationary groove being fixed while securely placing the buttress member in the stationary groove, at least a portion of the buttress member being proximal of the distal surface of the staple cartridge component,
  wherein at least a portion of the buttress member is in registration with the stationary overhang of the distal surface of the staple cartridge component when the buttress member is received in the stationary groove of the staple cartridge component.

7. The apparatus according to claim 6, wherein the portion of the buttress member extends radially outward from a peripheral portion of the buttress member.

* * * * *